United States Patent
Trayanova et al.

(10) Patent No.: US 11,922,630 B2
(45) Date of Patent: Mar. 5, 2024

(54) PREDICTING ATRIAL FIBRILLATION RECURRENCE AFTER PULMONARY VEIN ISOLATION USING SIMULATIONS OF PATIENT-SPECIFIC MAGNETIC RESONANCE IMAGING MODELS AND MACHINE LEARNING

(71) Applicant: THE JOHNS HOPKINS UNIVERSITY, Baltimore, MD (US)

(72) Inventors: Natalia Trayanova, Baltimore, MD (US); Rheeda Ali, Baltimore, MD (US); Julie Shade, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 399 days.

(21) Appl. No.: 17/425,540

(22) PCT Filed: Jan. 24, 2020

(86) PCT No.: PCT/US2020/015058
§ 371 (c)(1),
(2) Date: Jul. 23, 2021

(87) PCT Pub. No.: WO2020/154664
PCT Pub. Date: Jul. 30, 2020

(65) Prior Publication Data
US 2022/0101530 A1     Mar. 31, 2022

Related U.S. Application Data

(60) Provisional application No. 62/796,855, filed on Jan. 25, 2019.

(51) Int. Cl.
*G06T 7/11*     (2017.01)
*G16H 30/20*    (2018.01)
(Continued)

(52) U.S. Cl.
CPC .............. *G06T 7/11* (2017.01); *G16H 30/20* (2018.01); *G16H 30/40* (2018.01); *G16H 50/20* (2018.01);
(Continued)

(58) Field of Classification Search
CPC ......... G06T 2207/30048; G06T 7/0012; G06T 2207/10088; G06T 7/11;
(Continued)

(56) References Cited

U.S. PATENT DOCUMENTS

2007/0105217 A1* 5/2007 Pecora ..................... A61P 9/00
                                                      435/325
2010/0143317 A1* 6/2010 Pecora ................... A61K 35/16
                                                      424/93.72
(Continued)

FOREIGN PATENT DOCUMENTS

WO      2013140356 A1     9/2013

OTHER PUBLICATIONS

International Search Report and Written Opinion in corresponding International Application No. PCT/US2020/015058 dated May 25, 2020, 7 pages.

*Primary Examiner* — Ajibola A Akinyemi
(74) *Attorney, Agent, or Firm* — MH2 TECHNOLOGY LAW GROUP LLP

(57) ABSTRACT

A device may receive images of a patient, and may perform segmentation of surfaces on the images to create a 3D model. The device may identify normal tissue regions and atrial fibrosis (AF) regions in the 3D model, and may divide the 3D model into the normal tissue regions and the AF regions. The device may assign first cell and tissue properties to the normal tissue regions, and may assign second cell and tissue properties to the AF regions. The device may perform simulations on the normal tissue regions and the AD
(Continued)

regions, based on the first and second cell and tissue properties, to generate simulation results, and may extract first features from the simulation results. The device may extract second features from the images, and may process the first and second features, with a model, to select a feature that is predictive of atrial fibrillation recurrence.

20 Claims, 14 Drawing Sheets

(51) Int. Cl.
    *G16H 30/40* (2018.01)
    *G16H 50/20* (2018.01)
    *G16H 50/50* (2018.01)

(52) U.S. Cl.
    CPC ... *G16H 50/50* (2018.01); *G06T 2207/10088* (2013.01); *G06T 2207/20021* (2013.01); *G06T 2207/20081* (2013.01); *G06T 2207/20084* (2013.01); *G06T 2207/30048* (2013.01)

(58) Field of Classification Search
    CPC ........... G06T 2207/20081; G06T 7/149; G06T 2207/20084; G06T 7/12; G06T 2207/10132; G06T 2207/30004; G06T 7/174; G06T 2207/10081; G06T 2207/10072; G06T 7/10; G06T 2207/10104; G06T 2207/10108; G06T 7/0016; G06T 7/136; G06T 2200/04; G06T 2207/20128; G06T 7/143; G06T 2207/20112; G06T 2207/20124
    USPC ........................................................ 382/128
    See application file for complete search history.

(56) References Cited

U.S. PATENT DOCUMENTS

| | | |
|---|---|---|
| 2012/0071855 A1* | 3/2012 | Pecora ................. A61K 35/28 604/509 |
| 2015/0150643 A1 | 6/2015 | Trayanova et al. |
| 2017/0261584 A1 | 9/2017 | James et al. |
| 2017/0319278 A1 | 11/2017 | Trayanova et al. |
| 2018/0218497 A1 | 8/2018 | Golden et al. |
| 2021/0137384 A1* | 5/2021 | Robinson ............. A61B 5/0036 |

* cited by examiner

PREDICTING ATRIAL FIBRILLATION RECURRENCE AFTER PULMONARY VEIN ISOLATION USING SIMULATIONS OF PATIENT-SPECIFIC MAGNETIC RESONANCE IMAGING MODELS AND MACHINE LEARNING

RELATED APPLICATION

This application is a national stage entry from International Application No. PCT/US2020/015058, filed on Jan. 24, 2020, published as International Publication No. WO2020154664A1 on Jul. 30, 2020, which claims priority to U.S. Provisional Patent Application No. 62/796,855, filed on Jan. 25, 2019, the contents of both of which are hereby incorporated by reference herein in their entireties.

GOVERNMENT LICENSE RIGHTS

This invention was made with U.S. Government support under grant U01-HL141074, awarded by the National Institutes of Health. The U.S. Government has certain rights in the invention.

BACKGROUND

Catheter ablation of atrial fibrillation (AF) has become an increasingly frequent procedure performed in electrophysiology laboratories worldwide. Catheter ablation is most often performed for maintenance of sinus rhythm in patients with symptomatic, drug-refractory paroxysmal or persistent AF or as an initial rhythm control strategy in lieu of anti-arrhythmic drug therapy in patients with paroxysmal AF.

SUMMARY

According to some implementations, a method may include receiving clinical late gadolinium enhanced cardiac magnetic resonance imaging (LGE-MRI) images of a patient, and performing segmentation of epicardial and endocardial surfaces on the LGE-MRI images to create a patient-specific three-dimensional (3D) model for the patient. The method may include identifying normal tissue regions and atrial fibrosis regions in the 3D model based on intensity, and dividing the 3D model into the normal tissue regions and the atrial fibrosis regions. The method may include assigning first cell and tissue properties to the normal tissue regions according to a model of human cardiac myocyte and based on transverse and longitudinal conduction velocities, and assigning second cell and tissue properties to the atrial fibrosis regions according to a model of diffuse fibrosis with complete fibrotic remodeling. The method may include performing simulations on the normal tissue regions and the atrial fibrosis regions, based on the first cell and tissue properties and the second cell and tissue properties, to generate simulation results, and extracting first features from the simulation results based on the 3D model and based on a simulation protocol. The method may include extracting second features from the LGE-MRI images, and processing the first features and the second features, with a machine learning model, to select a feature, from at least one of the first features or the second features, that is predictive of atrial fibrillation recurrence. The method may include utilizing the feature to augment the simulation protocol for a future patient.

According to some implementations, a device may include one or more memories and one or more processors to receive clinical late gadolinium enhanced cardiac magnetic resonance imaging (LGE-MRI) images of a patient, and perform segmentation of epicardial and endocardial surfaces on the LGE-MRI images to create a patient-specific three-dimensional (3D) model for the patient. The one or more processors may identify normal tissue regions and atrial fibrosis regions in the 3D model based on intensity, and may divide the 3D model into the normal tissue regions and the atrial fibrosis regions. The one or more processors may assign first cell and tissue properties to the normal tissue regions according to a model of human cardiac myocyte and based on transverse and longitudinal conduction velocities, and may assign second cell and tissue properties to the atrial fibrosis regions according to a model of diffuse fibrosis with complete fibrotic remodeling. The one or more processors may perform simulations on the normal tissue regions and the atrial fibrosis regions, based on the first cell and tissue properties and the second cell and tissue properties, to generate simulation results, and may extract first features from the simulation results based on the 3D model and based on a simulation protocol. The one or more processors may extract second features from the LGE-MRI images, and may process the first features and the second features, with a machine learning model, to select a feature, from at least one of the first features or the second features, that is predictive of atrial fibrillation recurrence. The one or more processors may utilize the feature to augment the simulation protocol for a future patient.

According to some implementations, a non-transitory computer-readable medium may store one or more instructions that, when executed by one or more processors of a device, may cause the one or more processors to receive clinical late gadolinium enhanced cardiac magnetic resonance imaging (LGE-MRI) images of a patient, and perform segmentation of epicardial and endocardial surfaces on the LGE-MRI images to create a patient-specific three-dimensional (3D) model for the patient. The one or more instructions may cause the one or more processors to identify normal tissue regions and atrial fibrosis regions in the 3D model based on intensity, and divide the 3D model into the normal tissue regions and the atrial fibrosis regions. The one or more instructions may cause the one or more processors to assign first cell and tissue properties to the normal tissue regions according to a model of human cardiac myocyte and based on transverse and longitudinal conduction velocities, and assign second cell and tissue properties to the atrial fibrosis regions according to a model of diffuse fibrosis with complete fibrotic remodeling. The one or more instructions may cause the one or more processors to perform simulations on the normal tissue regions and the atrial fibrosis regions, based on the first cell and tissue properties and the second cell and tissue properties, to generate simulation results, and extract first features from the simulation results based on the 3D model and based on a simulation protocol. The one or more instructions may cause the one or more processors to extract second features from the LGE-MRI images, and process the first features and the second features, with a machine learning model, to select a feature, from at least one of the first features or the second features, that is predictive of atrial fibrillation recurrence. The one or more instructions may cause the one or more processors to utilize the feature to augment the simulation protocol for a future patient.

DETAILED DESCRIPTION

Figure 1A:
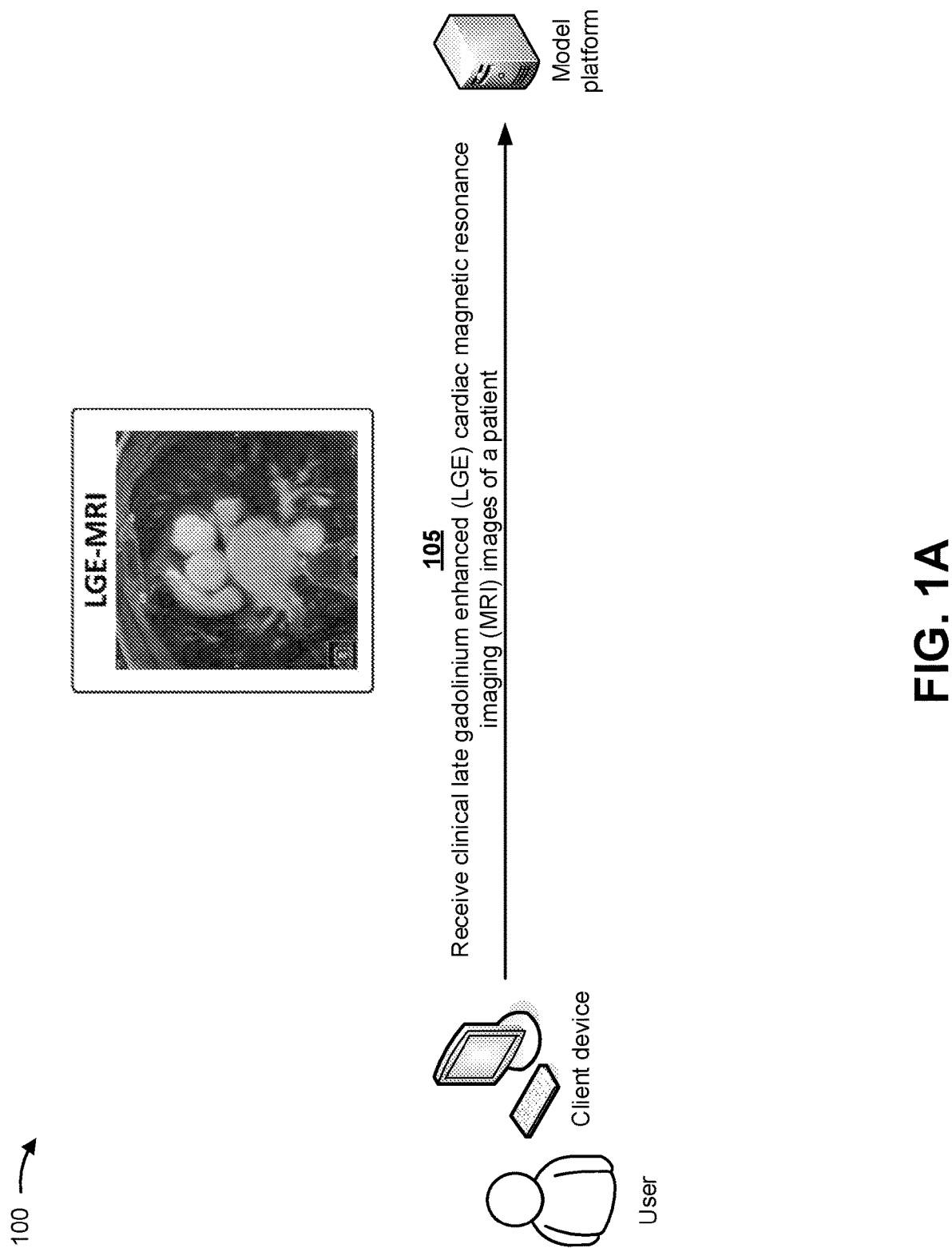
FIGS. 1A-1K are diagrams of one or more example implementations described herein.

The following detailed description of example implementations refers to the accompanying drawings. The same reference numbers in different drawings may identify the same or similar elements.

The increased efficacy of catheter ablation over antiarrhythmic drug therapy to maintain sinus rhythm has been demonstrated in several randomized, controlled trials and meta-analyses. Unfortunately, recurrent atrial fibrillation or atrial tachycardia after an index AF ablation procedure results in repeat ablation in 20 to 40% of patients. Patients with recurrent AF after catheter ablation present several issues, such as determining which patients should be considered for a second procedure and when should repeat ablation be performed, determining an optimal approach to ablation in a patient undergoing a repeat procedure, determining additional interventions that may reduce the likelihood of recurrence post-ablation, and/or the like. In patients with paroxysmal AF, pulmonary vein isolation has become an accepted treatment option with single procedure success rates of 60-80%. A repeat catheter ablation may be performed in about 30% of patients because of arrhythmia recurrence. However, a strategy has not been defined for the repeat catheter ablation. Thus, current systems waste computing resources (e.g., processing resources, memory resources, communication resources), networking resources, and/or the like associated with unsuccessfully repeating catheter ablation for patients, determining which patients should be considered for repeat catheter ablation, and/or the like.

Some implementations described herein provide a model platform that predicts atrial fibrillation recurrence after pulmonary vein isolation using simulations of patient-specific magnetic resonance imaging models and machine learning. For example, the model platform may receive clinical late gadolinium enhanced cardiac magnetic resonance imaging (LGE-MRI) images of a patient, and may perform segmentation of epicardial and endocardial surfaces on the LGE-MRI images to create a patient-specific three-dimensional (3D) model for the patient. The model platform may identify normal tissue regions and atrial fibrosis regions in the 3D model based on intensity, and may divide the 3D model into the normal tissue regions and the atrial fibrosis regions. The model platform may assign first cell and tissue properties to the normal tissue regions according to a model of human cardiac myocyte and based on transverse and longitudinal conduction velocities, and may assign second cell and tissue properties to the atrial fibrosis regions according to a model of diffuse fibrosis with complete fibrotic remodeling. The model platform may perform simulations on the normal tissue regions and the atrial fibrosis regions, based on the first cell and tissue properties and the second cell and tissue properties, to generate simulation results, and may extract first features from the simulation results based on the 3D model and based on a simulation protocol. The model platform may extract second features from the LGE-MRI images, and may process the first features and the second features, with a machine learning model, to select a feature, from at least one of the first features or the second features, that is predictive of atrial fibrillation recurrence. The model platform may utilize the feature to augment the simulation protocol for a future patient.

In this way, the model platform predicts atrial fibrillation recurrence after pulmonary vein isolation using simulations of patient-specific magnetic resonance imaging models and machine learning. The model platform may predict whether such a pulmonary vein isolation will be successful, and whether additional lesions are needed in a patient's atria so that the patient becomes free of AF. The model platform may construct a patient-specific model of the patient's atria from contrast-enhanced MRI images (e.g., scans), and may perform simulations to determine types of arrhythmia that may exist in the patient. The model platform may provide the MRI images and results of the simulations to a machine learning model that extracts a set of features that is most predictive of AF recurrence. Once trained, the machine learning model may predict, with a high level of accuracy, whether the isolation of the pulmonary veins in the patient will succeed in terminating AF, or whether a physician will need to conduct ablation in fibrotic parts of the patient's atria. Thus, the model platform conserves computing resources (e.g., processing resources, memory resources, communication resources), networking resources, and/or the like that would otherwise be wasted in unsuccessfully repeating catheter ablation for patients, determining which patients should be considered for repeat catheter ablation, and/or the like.

FIGS. 1A-1K are diagrams of one or more example implementations 100 described herein. As shown in FIG. 1A, a client device may be associated with a model platform. The client device 210 may include a mobile device, a computer, and/or the like. The client device may be associated with an MRI device that captures MRI images of a patient, may store the MRI images of the patient, may provide the MRI images to the model platform, and/or the like. In some implementations, the MRI images may include clinical late gadolinium enhanced (LGE) cardiac MRI images (e.g., LGE-MRI images) of the patient. The model platform may include a platform that predicts atrial fibrillation recurrence after pulmonary vein isolation using simulations of patient-specific magnetic resonance imaging models and machine learning, in a manner described herein.

As further shown in FIG. 1A, and by reference number 105, the model platform may receive, from the client device (e.g., or from the MRI device), the clinical LGE cardiac MRI images of the patient. In some implementations, the LGE-MRI images of the patient may be stored in a data structure (e.g., a database, a table, a list, and/or the like) associated with the model platform.

Figure 1B:
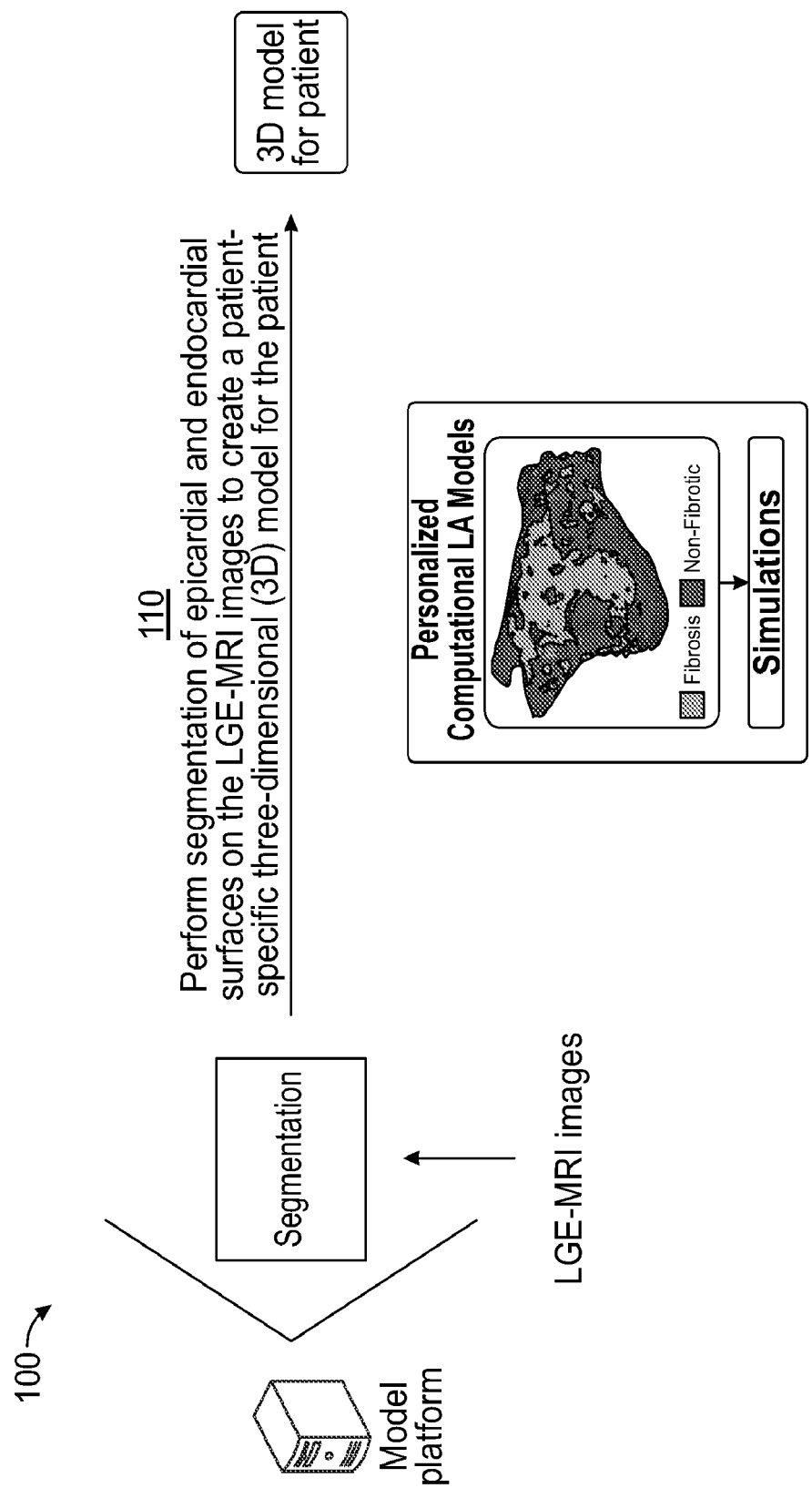

As shown in FIG. 1B, and by reference number 110, the model platform may perform segmentation of epicardial and endocardial surfaces on the LGE-MRI images to create a patient-specific three-dimensional (3D) model for the patient. In some implementations, the model platform may utilize automatic and semi-automatic segmentation models (e.g., using a short-axis view) to perform the segmentation of the epicardial and endocardial surfaces on the LGE-MRI images and to create the 3D model for the patient. In some implementations, the automatic and semi-automatic segmentation models may include a level-set-based active contour model, a localized region-based active contour model, a seeded region growing model, a K-means clustering model, a fuzzy C-means clustering model, a maximum entropy model, a balanced histogram thresholding model, a maximum variance model, and/or the like.

In some implementations, the model platform may train the automatic and semi-automatic segmentation models with historical data (e.g., historical LGE-MRI images) to enable the automatic and semi-automatic segmentation models to create patient-specific 3D models for patients. In some implementations, the model platform may separate the historical data into a training set, a validation set, a test set, and/or the like. The training set may be utilized to train the automatic and semi-automatic segmentation models. The validation set may be utilized to validate results of the trained automatic and semi-automatic segmentation models. The test set may be utilized to test operation of the trained automatic and semi-automatic segmentation models.

In some implementations, the model platform may train the automatic and semi-automatic segmentation models using, for example, an unsupervised training procedure and based on the historical data. For example, the model platform may perform dimensionality reduction to reduce the historical data to a minimum feature set, thereby reducing resources (e.g., processing resources, memory resources, and/or the like) to train the automatic and semi-automatic segmentation models, and may apply a classification technique to the minimum feature set.

In some implementations, the model platform may use a logistic regression classification technique to determine a categorical outcome (e.g., patient-specific 3D models). Additionally, or alternatively, the model platform may use a naïve Bayesian classifier technique. In this case, the model platform may perform binary recursive partitioning to split the historical data into partitions and/or branches, and use the partitions and/or branches to determine outcomes (e.g., patient-specific 3D models). Based on using recursive partitioning, the model platform may reduce utilization of computing resources relative to manual, linear sorting and analysis of data points, thereby enabling use of thousands, millions, or billions of data points to train the automatic and semi-automatic segmentation models, which may result in more accurate models than using fewer data points.

Additionally, or alternatively, the model platform may use a support vector machine (SVM) classifier technique to generate a non-linear boundary between data points in the training set. In this case, the non-linear boundary is used to classify test data into a particular class.

Additionally, or alternatively, the model platform may train the automatic and semi-automatic segmentation models using a supervised training procedure that includes receiving input to the automatic and semi-automatic segmentation models from a subject matter expert, which may reduce an amount of time, an amount of processing resources, and/or the like to train the automatic and semi-automatic segmentation models relative to an unsupervised training procedure.

In some implementations, the model platform may use one or more other model training techniques, such as a latent semantic indexing technique, and/or the like. For example, the model platform may perform an artificial neural network processing technique (e.g., using a two-layer feedforward neural network architecture, a three-layer feedforward neural network architecture, and/or the like) to perform pattern recognition with regard to patterns of the historical data. In this case, using the artificial neural network processing technique may improve an accuracy of the trained automatic and semi-automatic segmentation models generated by the model platform by making the automatic and semi-automatic segmentation models more robust to noisy, imprecise, or incomplete data, and by enabling the model platform to detect patterns and/or trends undetectable to human analysts or systems using less complex techniques.

In some implementations, rather than training the automatic and semi-automatic segmentation models, the model platform may obtain the trained automatic and semi-automatic segmentation models from another system or device that trained the automatic and semi-automatic segmentation models to generate the trained automatic and semi-automatic segmentation models. In this case, the model platform may provide the other system or device with the historical data for use in training the automatic and semi-automatic segmentation models, and may provide the other system or device with updated historical data to retrain the automatic and semi-automatic segmentation models in order to update the trained automatic and semi-automatic segmentation models.

Figure 1C:
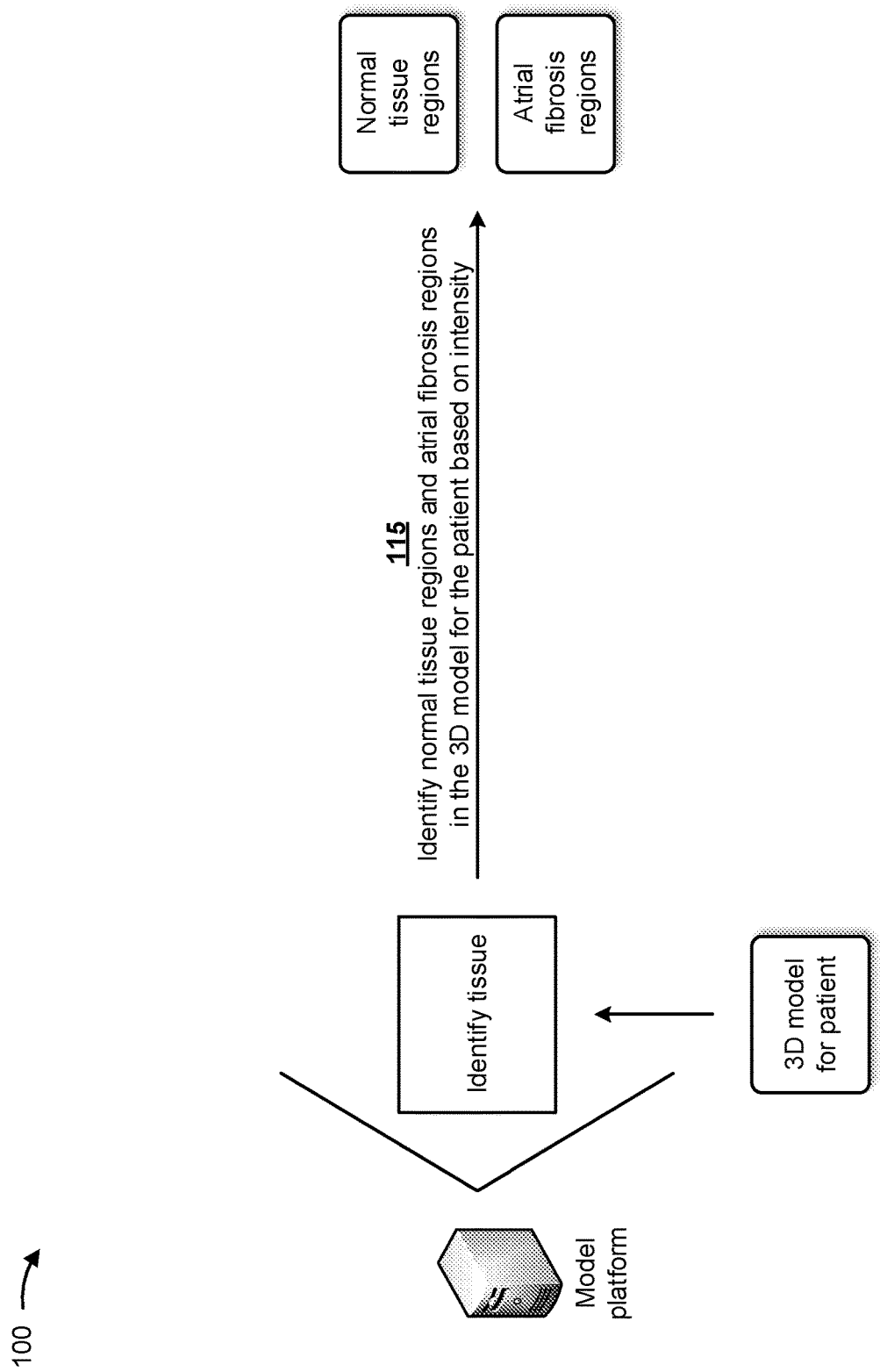

As shown in FIG. 1C, and by reference number 115, the model platform may identify normal tissue regions and atrial fibrosis regions in the 3D model for the patient based on intensity observed in the LGE-MRI images. In some implementations, the model platform may utilize contrast enhancement of the LGE-MRI images (e.g., via gadolinium) to visualize and quantify the normal tissue regions and the atrial fibrosis regions. The contrast enhancement of the LGE-MRI images may enable in-vivo visualization of myocardial fibrotic tissue, non-invasive evaluation of atrial fibrosis, and/or the like.

Figure 1D:
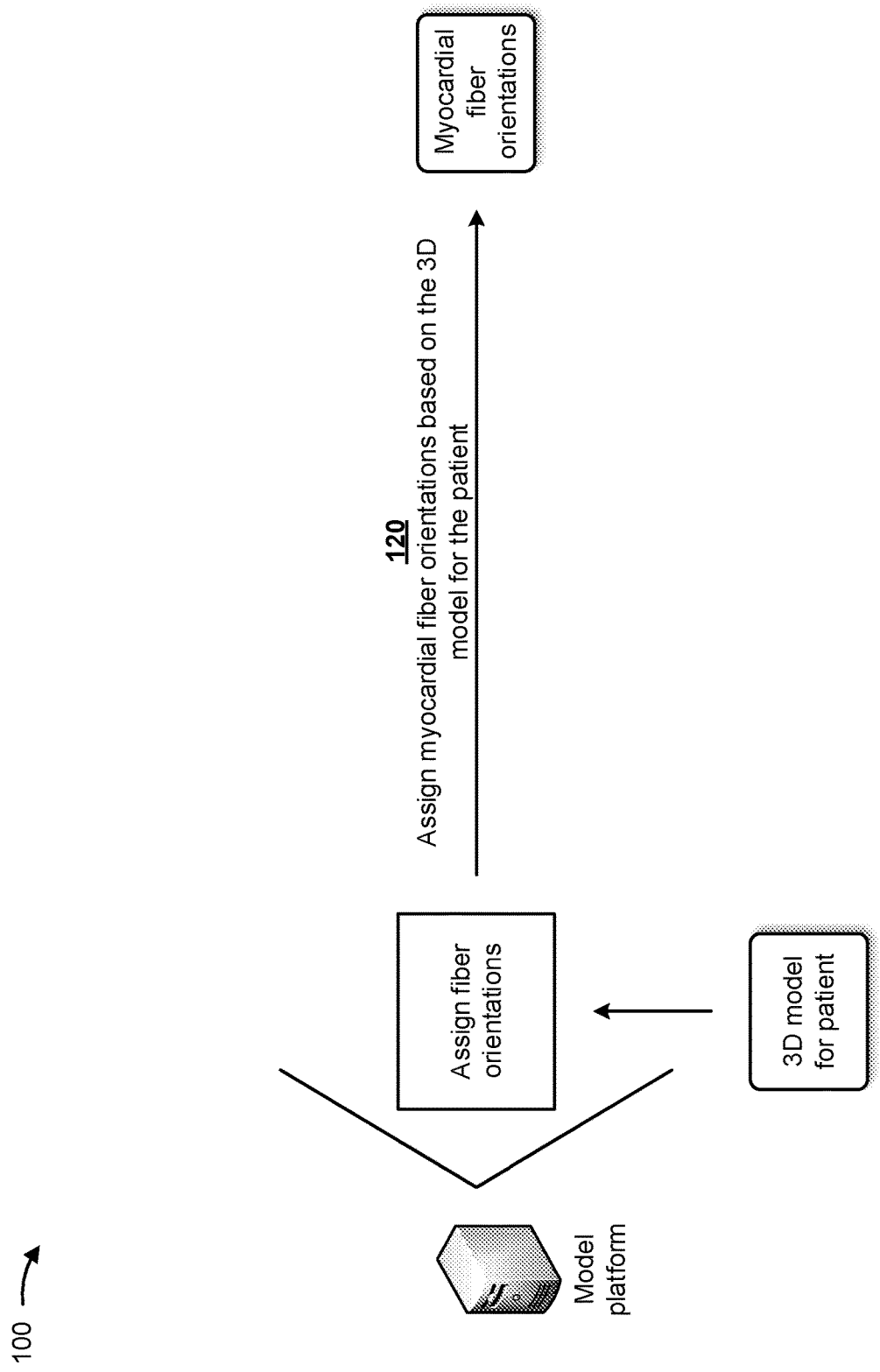

As shown in FIG. 1D, and by reference number 120, the model platform may assign myocardial fiber orientations based on the 3D model for the patient. In some implementations, the model platform may utilize a rule-based model to assign the myocardial fiber orientations based on the 3D model. In some implementations, the model platform may utilize a rule-based model and an atlas-based model to assign the myocardial fiber orientations based on the 3D model. In such implementations, the model platform may utilize an automated transfer of predefined landmarks from an average atrial geometry to a personalized atrial geometry and a prior definition of certain rules. The rule-based model may include a Laplace-Dirichlet rule-based model, and the atlas-based model may include an atlas-based geometry pipeline model.

In some implementations, the model platform may train the rule-based and atlas-based models with historical data (e.g., historical 3D models for patients) to enable the rule-based and atlas-based models to assign myocardial fiber orientations based on the 3D models for the patients. For example, the model platform may train the rule-based and atlas-based models in a manner similar to the automatic and semi-automatic segmentation models described above in connection with FIG. 1C. In some implementations, rather than training the rule-based and atlas-based models, the model platform may obtain the rule-based and atlas-based models from another system or device that trained the rule-based and atlas-based models. In such implementations, the model platform may provide the other system or device with historical data for use in training the rule-based and atlas-based models, and may provide the other system or device with updated historical data to retrain the rule-based and atlas-based models in order to update the rule-based and atlas-based models.

Figure 1E:
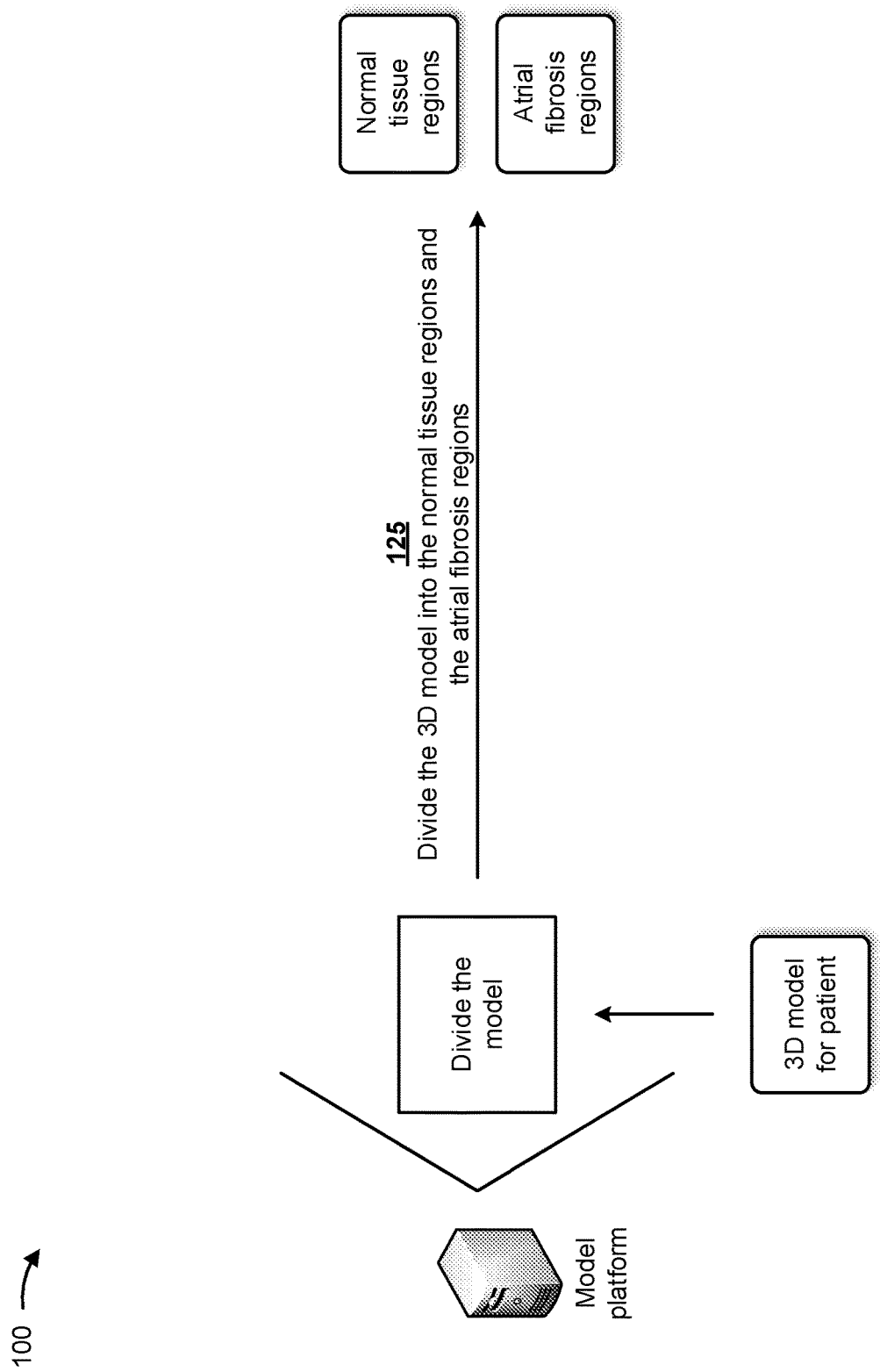

As shown in FIG. 1E, and by reference number 125, the model platform may divide the 3D model into normal tissue regions and atrial fibrosis regions. In some implementations, the model platform may utilize the identified normal tissue regions and atrial fibrosis regions in the 3D model, as described above in connection with FIG. 1C, to divide the 3D model into the normal tissue regions and the atrial fibrosis regions.

Figure 1F:
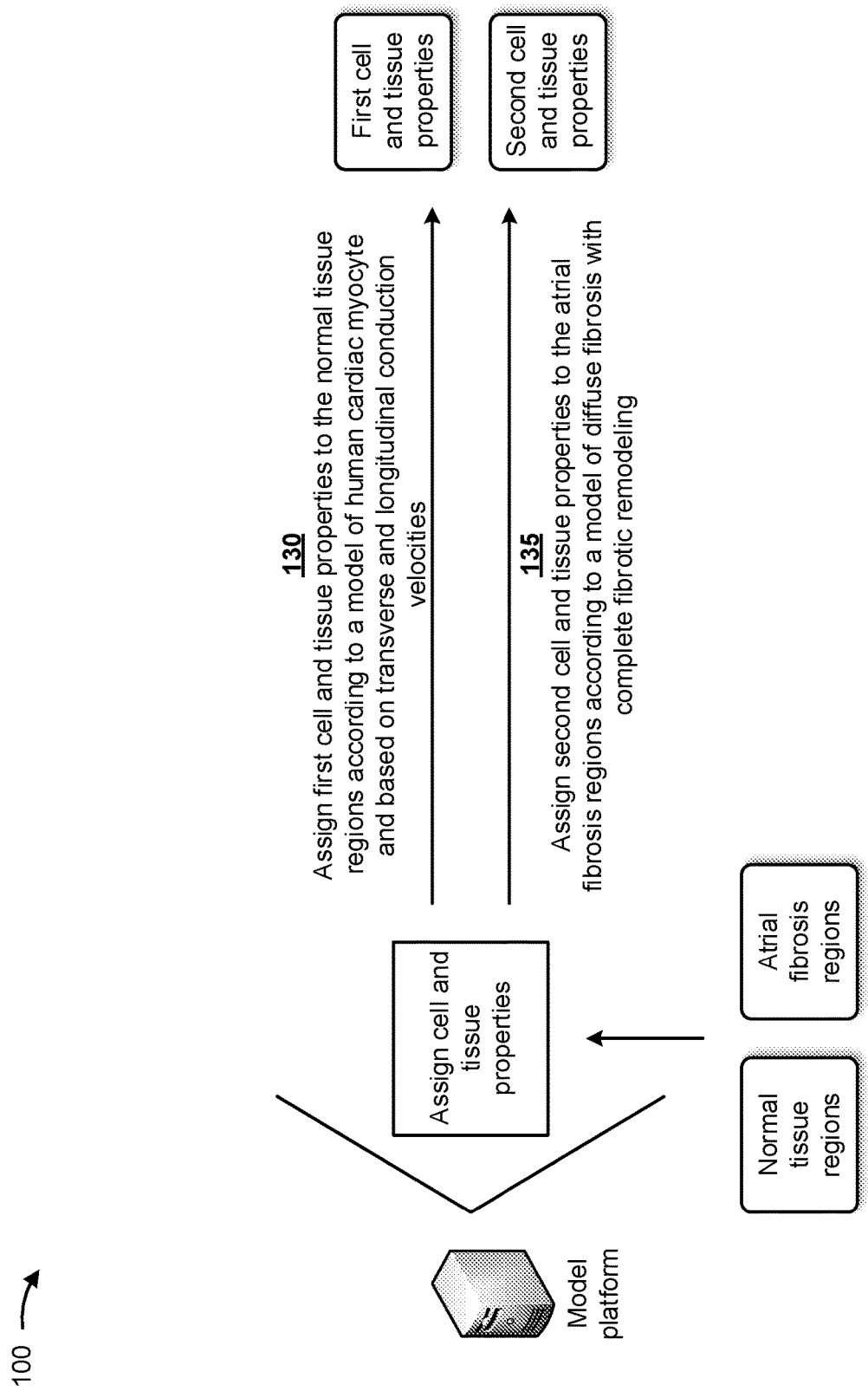

As shown in FIG. 1F, and by reference number 130, the model platform may assign cell and tissue properties to the normal tissue regions according to a model of human cardiac myocyte and based on transverse and longitudinal conduction velocities in the normal tissue regions. In some implementations, the model of human cardiac myocyte may include a Noble ventricular cell model, a Luo-Rudy Phase I ventricular myocyte model, a Luo-Rudy Phase II ventricular myocyte model, and/or the like.

In some implementations, the model platform may train the model of human cardiac myocyte with historical data (e.g., historical data associated with normal tissue regions) to enable the model of human cardiac myocyte to assign cell and tissue properties to the normal tissue regions. For example, the model platform may train the model of human cardiac myocyte in a manner similar to the automatic and semi-automatic segmentation models described above in connection with FIG. 1C. In some implementations, rather than training the model of human cardiac myocyte, the model platform may obtain the model of human cardiac myocyte from another system or device that trained the model of human cardiac myocyte. In such implementations, the model platform may provide the other system or device with historical data for use in training the model of human cardiac myocyte, and may provide the other system or device with updated historical data to retrain the model of human cardiac myocyte in order to update the model of human cardiac myocyte.

As further shown in FIG. 1F, and by reference number 135, the model platform may assign cell and tissue properties to the atrial fibrosis regions according to a model of diffuse fibrosis with complete fibrotic remodeling. In some implementations, the model of diffuse fibrosis may include a ten Tusscher-Noble-Noble-Panfilov (TNNP) model for human ventricular tissue. In some implementations, the model platform may train the model of diffuse fibrosis with historical data (e.g., historical data associated with atrial fibrosis regions) to enable the model of diffuse fibrosis to assign cell and tissue properties to the atrial fibrosis regions. For example, the model platform may train the model of diffuse fibrosis in a manner similar to the automatic and semi-automatic segmentation models described above in connection with FIG. 1C. In some implementations, rather than training the model of diffuse fibrosis, the model platform may obtain the model of diffuse fibrosis from another system or device that trained the model of diffuse fibrosis. In such implementations, the model platform may provide the other system or device with historical data for use in training the model of diffuse fibrosis, and may provide the other system or device with updated historical data to retrain the model of diffuse fibrosis in order to update the model of diffuse fibrosis.

Figure 1G:
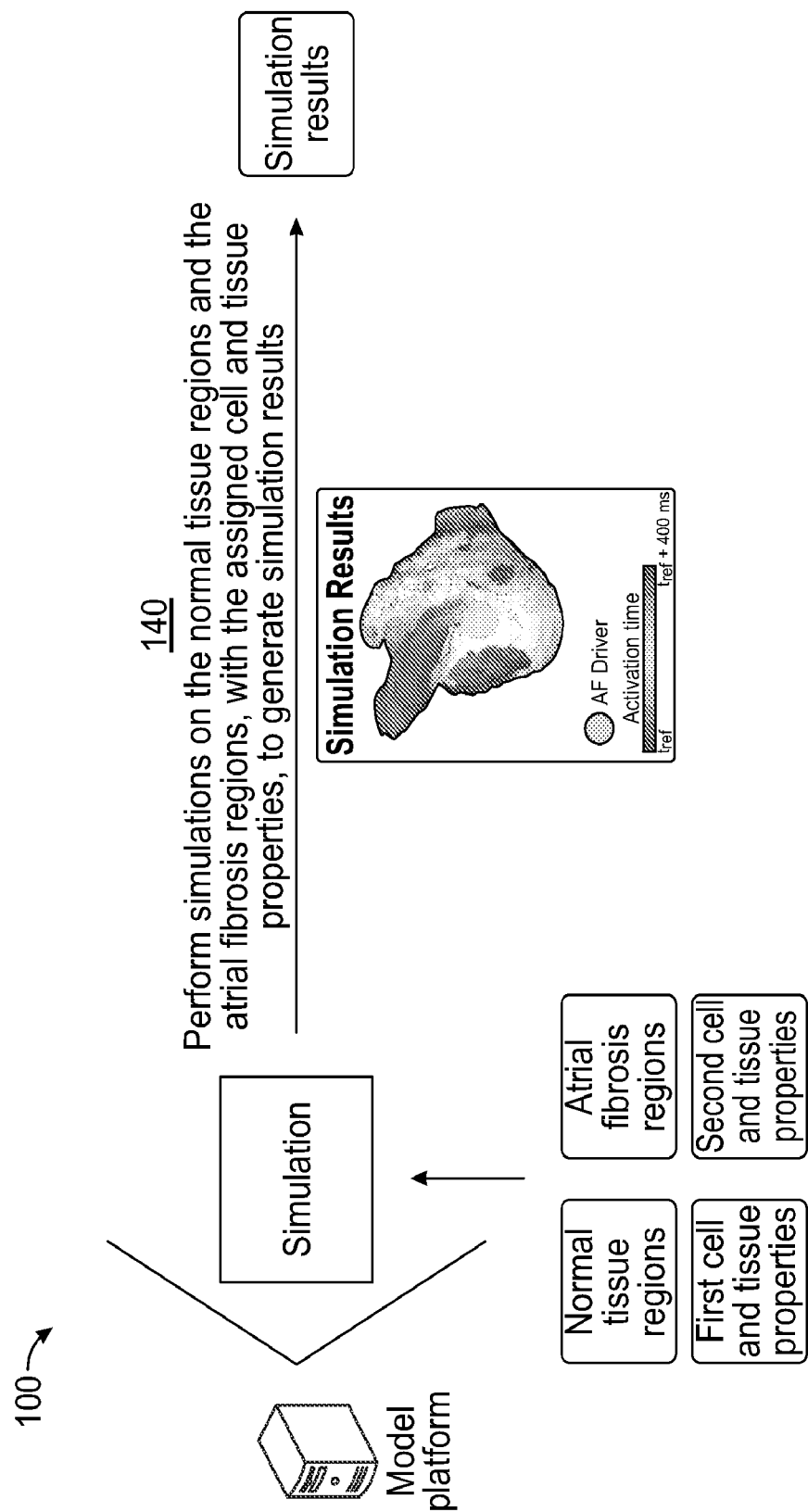

As shown in FIG. 1G, and by reference number 140, the model platform may perform simulations on the normal tissue regions and the atrial fibrosis regions, with the assigned cell and tissue properties, to generate simulation results. In some implementations, the simulations may include simulations of AF sites in the 3D model with geometry and fibrosis distribution from pre-ablation LGE-MRI images. In some implementations, the simulation results may include information indicating types of arrhythmia that may exist in the patient, a quantity of pacing sites that induced atrial fibrillation, a quantity of re-entrant drivers (RDs) outside a pulmonary vein ostium, a predictive capability if subsets of pacing locations, and/or the like.

Figure 1H:
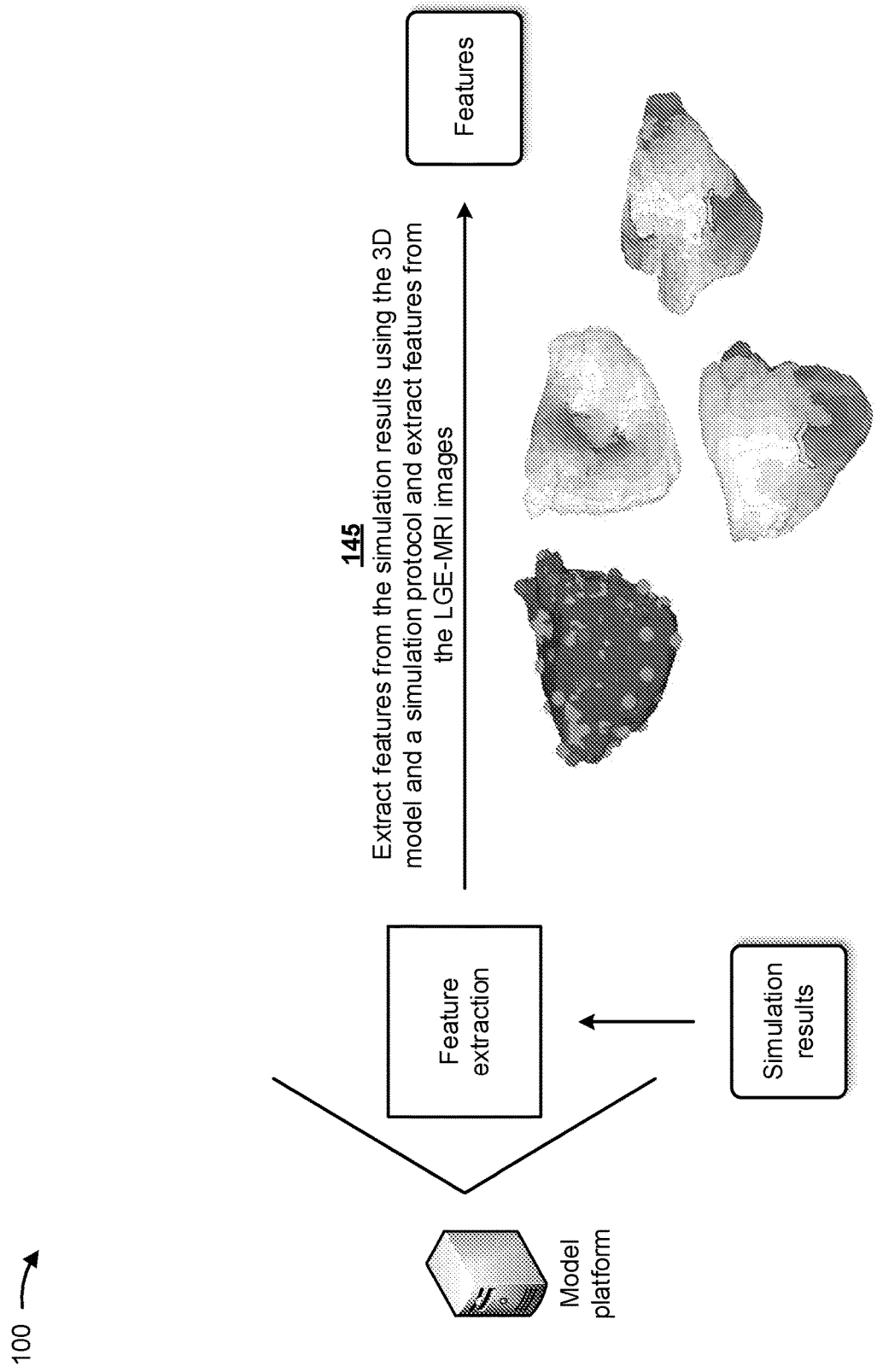

As shown in FIG. 1H, and by reference number 145, the model platform may extract features from the simulation results using the 3D model and a simulation protocol and may extract features from the LGE-MRI images. In some implementations, the features may be associated with AF recurrence. In some implementations, the features associated with the simulation results may include features indicating a quantity of pacing sites that induced atrial fibrillation, a quantity of RDs outside a pulmonary vein ostium, a predictive capability if subsets of pacing locations, and/or the like. In some implementations, the features associated with the LGE-MRI images may include features indicating entropy (e.g., disorder), fibrosis border complexity (e.g., quantified by fractal dimensions), percent fibrosis, and/or the like.

Figure 1I:
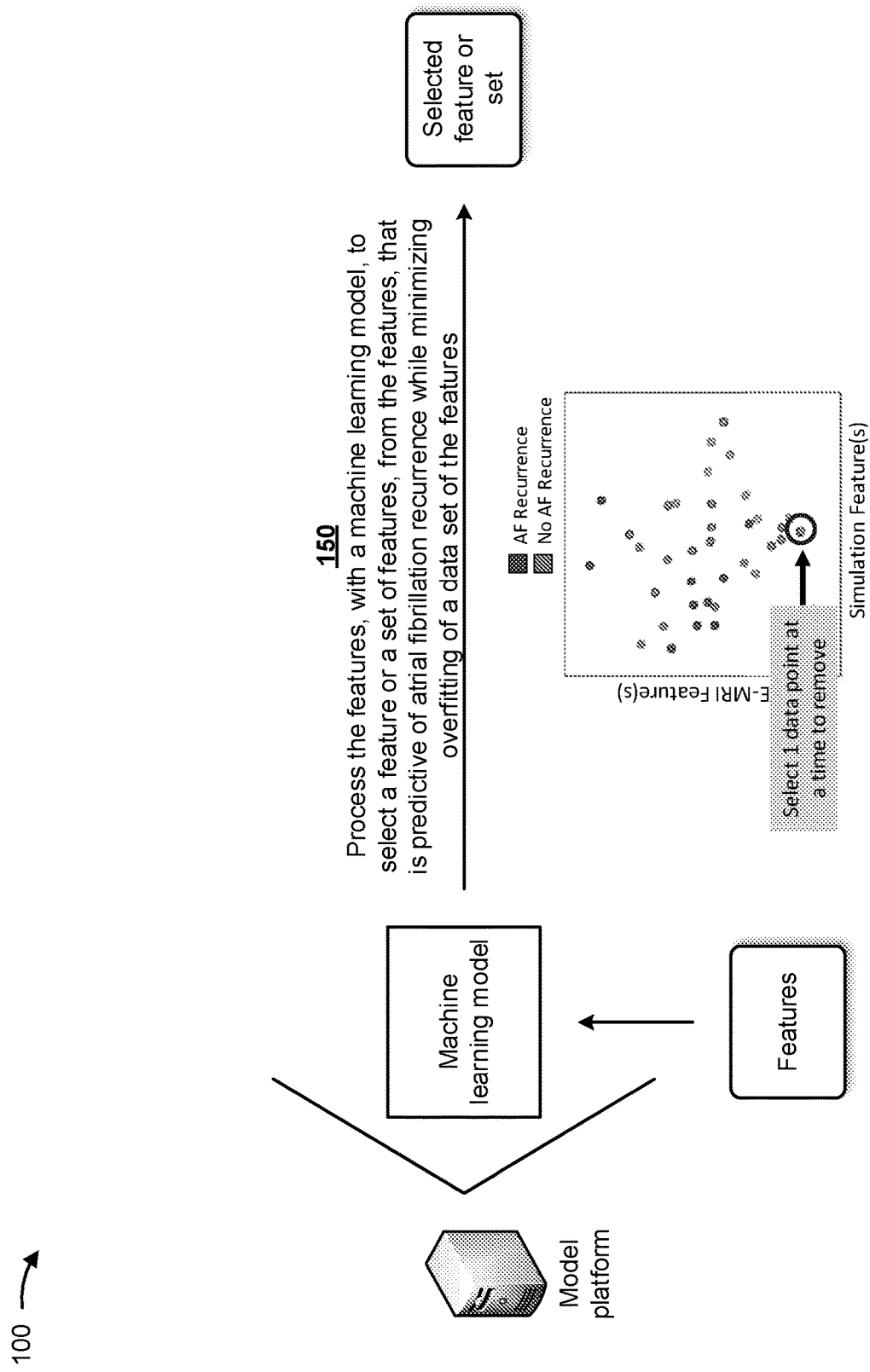

As shown in FIG. 1I, and by reference number 150, the model platform may process the features, with a machine learning model, to select a feature or a set of features, from the features, predictive of AF recurrence while minimizing overfitting of a data set of the features. In some implementations, the machine learning model may include a model (e.g., a classifier model, a random forest (with k-fold cross validation) model, and/or the like) that selects features predictive of AF recurrence. In some implementations, the model platform may utilize a ten-fold nested cross-validation to train, validate, and test the machine learning model. The model platform may utilize random forest models for unbiased feature selection, and may then train a quadratic discriminant analysis (QDA) classifier with the selected features to predict a probability of AF recurrence after pulmonary vein ostium.

In some implementations, the model platform may perform a training operation on the machine learning model with historical data (e.g., historical data indicating features extracted from simulation results of other patients, features extracted from LGE-MRI images of other patients, and/or the like) to enable the machine learning model to select features predictive of AF recurrence. For example, the model platform may train the machine learning model in a manner similar to the automatic and semi-automatic segmentation models described above in connection with FIG. 1C. In some implementations, rather than training the machine learning model, the model platform may obtain the machine learning model from another system or device that trained the machine learning model. In such implementations, the model platform may provide the other system or device with historical data for use in training the machine learning model, and may provide the other system or device with updated historical data to retrain the machine learning model in order to update the machine learning model.

In some implementations, the machine learning model may utilize the features extracted from simulation and the features extracted from the LGE-MRI images to identify data points that indicate AF recurrence, data points that indicate no AF recurrence, data that indicate a likelihood of AF recurrence, and/or the like. The model platform may select and remove one data point from the data points, and may retrain the machine learning model with the remaining data points. The model platform may analyze outputs of the retrained machine learning models, and may identify an optimum retrained machine learning model based on the outputs. The model platform may utilize the optimum retrained machine learning model as a final machine learning model to utilize for predicting catheter ablations efficiency.

Figure 1J:
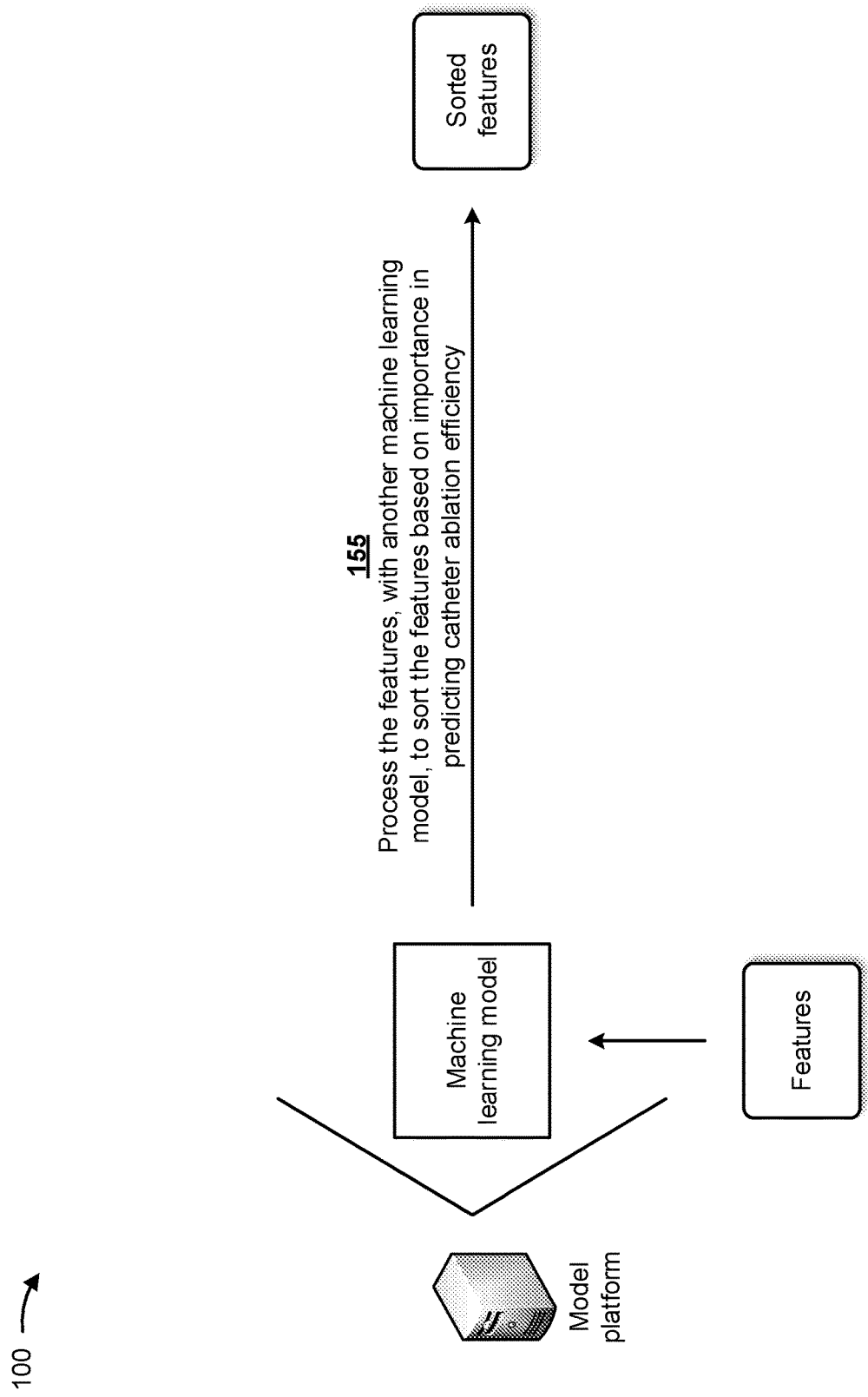

As shown in FIG. 1J, and by reference number 155, the model platform may process the features, with another machine learning model, to sort the features based on importance in predicting catheter ablation efficiency. In some implementations, the other machine learning model may include a regression analysis model that sorts the features based on importance in predicting catheter ablation efficiency.

In some implementations, the model platform may perform a training operation on the other machine learning model with historical data (e.g., historical data indicating features extracted from simulation results of other patients, features extracted from LGE-MRI images of other patients, and/or the like) to enable the other machine learning model to sort the features based on importance in predicting catheter ablation efficiency. For example, the model platform may train the other machine learning model in a manner similar to the automatic and semi-automatic segmentation models described above in connection with FIG. 1C. In some implementations, rather than training the other machine learning model, the model platform may obtain the other machine learning model from another system or device that trained the other machine learning model. In such implementations, the model platform may provide the other system or device with historical data for use in training the other machine learning model, and may provide the other system or device with updated historical data to retrain the other machine learning model in order to update the other machine learning model.

Figure 1K:
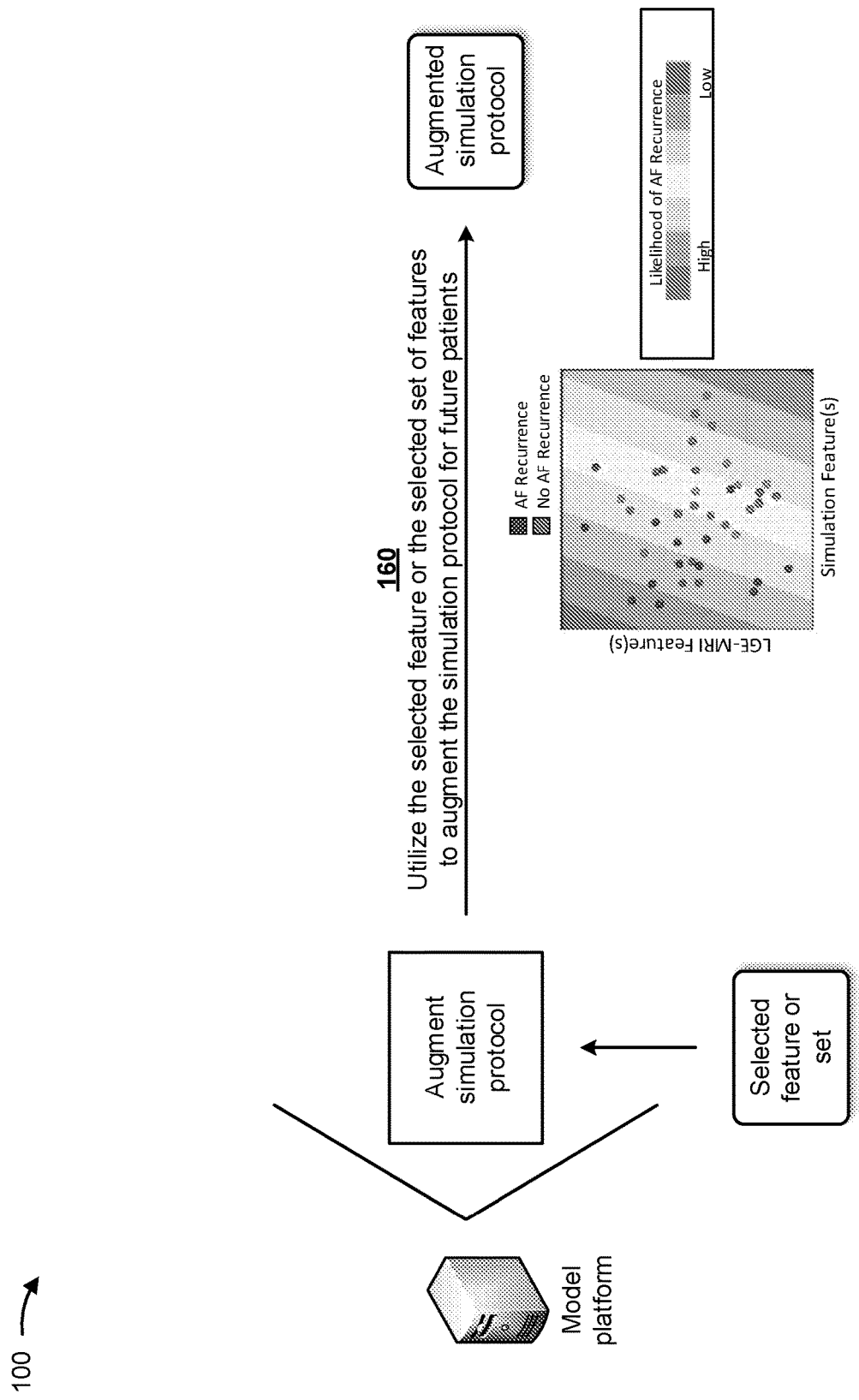

As shown in FIG. 1K, and by reference number 160, the model platform may utilize the selected feature or the selected set of features to augment the simulation protocol for future patients. In some implementations, the model platform may utilize the selected feature or the selected set of features to predict whether isolation of the pulmonary veins will be successful and whether additional lesions are needed in a patient's atria so that the patient becomes free of AF.

In this way, the model platform predicts AF recurrence after pulmonary vein isolation in a patient, which conserves computing resources (e.g., processing resources, memory resources, communication resources, and/or the like), networking resources, hospital resources (e.g., a heart monitor, a breathing apparatus, and/or the like), and/or the like, that would otherwise be wasted in performing unnecessary procedures on the patient, unsuccessfully repeating catheter ablation for patients, determining which patients should be considered for repeat catheter ablation, and/or the like.

As indicated above, FIGS. 1A-1K are provided merely as examples. Other examples may differ from what is described with regard to FIGS. 1A-1K. The number and arrangement of devices and networks shown in FIGS. 1A-1K are provided as an example. In practice, there may be additional devices and/or networks, fewer devices and/or networks, different devices and/or networks, or differently arranged devices and/or networks than those shown in FIGS. 1A-1K. Furthermore, two or more devices shown in FIGS. 1A-1K may be implemented within a single device, or a single device shown in FIGS. 1A-1K may be implemented as multiple, distributed devices. Additionally, or alternatively, a set of devices (e.g., one or more devices) of FIGS. 1A-1K may perform one or more functions described as being performed by another set of devices of FIGS. 1A-1K.

Example Implementation

The following paragraphs provide an example implementation associated with the model platform. Pulmonary vein isolation (PVI) is an effective treatment strategy for patients with atrial fibrillation (AF), but many experience AF recurrence and require repeat ablation procedures. The goal of this study was to develop and evaluate a methodology which combines machine learning (ML) and personalized computational modeling to predict, prior to PVI, which patients are most likely to experience AF recurrence after PVI.

This single-center retrospective proof-of-concept study included 32 patients with documented paroxysmal AF who underwent PVI and had pre-procedural late gadolinium enhanced magnetic resonance imaging (LGE-MRI). For each patient, a personalized computational model of the left atrium simulated AF induction via rapid pacing. Features were derived from LGE-MRI images and from simulation results. The most predictive features were used as input to a quadratic discriminant analysis ML classifier, which was trained, optimized, and evaluated with 10-fold nested cross validation to predict the probability of AF recurrence post-PVI.

The ML classifier predicted the probability of AF recurrence with an average validation sensitivity and specificity of 82% and 89%, respectively, and a validation AUC of 0.82. Dissecting the relative contributions of the simulation results and imaging to the predictive capability of the ML classifier, we found that when only features from the simulation results were used to train the ML classifier, its performance remained similar (validation AUC=0.81). However, when only imaging features were used to train it, the validation AUC became significantly lower (0.47).

ML and personalized computational modeling can be used together to accurately predict AF recurrence after PVI, even when the patient cohort is small. Including imaging features in the classifier did not significantly improve its predictive capability.

Atrial fibrillation (AF) is the most common cardiac arrhythmia, with paroxysmal atrial fibrillation (PxAF) accounting for around 25% of AF cases. Untreated AF leads to increased risk of stroke and heart failure. For many PxAF patients, pulmonary vein isolation (PVI) ablation is a successful treatment strategy. However, in a meta-analysis of PVI outcomes, only 78% of patients were free from AF at 12 months. Patients who experience AF recurrence may require repeat PVI or additional substrate modification in the fibrotic left atrium (LA). A methodology which identifies, prior to PVI, patients who are likely to experience post-PVI AF recurrence would allow development of targeted ablation strategies for these patients, reducing redo procedures and decreasing the risk of morbidity and mortality.

Given the importance of early and effective intervention for atrial arrhythmias, many machine learning (ML)-based healthcare technologies have focused on AF detection and clinical outcome prediction. There have been several attempts to use ML to predict AF recurrence after ablation, including a study which used deep learning-based LA shape analysis, and another which used ML on imaging and clinical biomarkers to predict cryo-balloon PVI outcomes. However, ample experimental and clinical evidence supports the primary role of fibrosis remodeling in the atria in the pathophysiology of AF, which thus far has not been accounted for in ML approaches aimed at predicting AF recurrence after PVI.

Atrial fibrosis promotes the initiation and perpetuation of re-entrant activity underlying AF by disrupting conduction and establishing regions of pro-fibrillatory substrate. However, it remains unknown to what degree the patient-specific fibrosis distribution prior to ablation is a contributing factor to AF recurrence after PVI. Personalized biophysically-detailed computational models of the atria based on the patient's late gadolinium enhanced magnetic resonance imaging (LGE-MRI), which visualizes the personalized fibrosis distribution, allow for clinically-validated, non-invasive investigation of the susceptibility of a patient's fibrotic substrate to sustaining reentrant activity. Such atrial models of arrhythmogenic propensity may have potential to predict the probability of AF recurrence after PVI, but reducing hundreds of thousands of transmembrane voltage measurements over thousands of milliseconds to meaningful predictive features is a difficult task. In addition, mechanistic modeling does not explicitly consider clinical biomarkers or quantitative measures of the structural remodeling derived from raw imaging data. ML classifiers are ideal for identifying predictive patterns in high-dimensional data and combining predictive features derived from multiple sources, thus we hypothesize that a combination of ML and mechanistic modeling may provide accurate prediction of AF recurrence after PVI.

In this proof-of-concept study, we develop a novel approach that combines mechanistic computational modeling and ML to predict the individual patient's probability of AF recurrence post-PVI using the patient's pre-procedure LGE-MRI scans. We show that this approach results in an ML classifier that achieves high validation sensitivity and specificity even when even when the patient cohort available for training is small.

In this institutional review board-approved retrospective study, we present a novel predictor of AF recurrence post-PVI using ML and personalized LA computational models in patients with PxAF and fibrosis on LGE-MRI. In a cohort of 32 patients, we evaluated the predictive capability of this classifier. In doing so, for each patient, a personalized computational model of the LA was constructed to simulate AF induction via rapid pacing. Features were derived from LGE-MRI images and from the simulation results to serve as input into a quadratic discriminant analysis ML classifier. Features from the simulation results were chosen in two ways: i) they were based on general knowledge of AF dynamics, and ii) they were left to be chosen by the ML training algorithm, unsupervised. The classifier was trained, optimized, and evaluated with 10-fold nested cross validation. Finally, we assessed the capabilities of ML risk predictors that used features from the simulation results only and imaging only, thus distinguishing the relative contributions to the overall predictive capability.

This study included adult patients from a single center with documented PxAF who received pre-procedural LGE-MRI scans and underwent PVI ablation between December 2011 and December 2015. PxAF was defined as an episode of AF that terminated spontaneously or with intervention within 7 days. Patients were excluded from the study if their LGE-MRI had motion or breathing artifact or if the myocardium was not correctly nulled, resulting in insufficient visualization of the LA geometry and fibrosis distribution for model reconstruction and ML. 32 patients were included in the study.

All patients were observed overnight in the hospital for hemodynamic monitoring and resumption of anticoagulation. Routine follow-up with electrocardiograms (ECGs) and clinical assessment was performed at 3, 6, and 12 months. Additional follow-up for symptomatic patients was performed if necessary, including Holter monitoring. Any recurrence of AF/atrial tachycardia (AT) documented by ECG or a device-recording system lasting ≥30 seconds, outside of a 3-month post-procedure blanking period, was considered recurrence.

12 (38%) patients experienced AF recurrence in the follow-up period. All patients had PVI with either radiofrequency (RF) or cryo-balloon ablation. 28 (88%) patients underwent circumferential linear RF ablation around the left and right pulmonary veins. The other 4 (12%) patients had cryo-balloon ablation performed with a 23 or 28 mm cryo-balloon. The median time between the PVI procedure and last date of follow-up was 366 days (IQR: 365-467 days). The median time to reported AF recurrence was 310 days (IQR: 204-381 days).

LGE-MRI scans were acquired using a 1.5 T Avanto MR system for the purpose of visualizing and reconstructing the atrial geometry and fibrosis distribution. Scans were performed in the axial orientation 10-27 min following 0.2 mmol/kg of gadobenate dimeglumine contrast agent using a fat-saturated 3-dimensional (3D) IR-prepared fast spoiled gradient recalled echo sequence, with electrocardiogram-triggered and respiratory navigator gating. Image resolution was 1.25×1.25×2.5 mm.

Briefly, the LA epicardial and endocardial walls were manually delineated on the LGE-MRI using ITK-snap. Fibrotic voxels were classified with image intensity ratio greater than 1.22. High-resolution tetrahedral finite-element meshes were generated from the up-sampled segmented images. Realistic myocardial fiber orientations were incorporated using a diffeomorphic mapping technique from an atlas geometry.

Electrophysiological properties were assigned to non-fibrotic and fibrotic tissue in the geometric models as described previously. Specifically, a human chronic AF action potential model with modifications to fit clinical monophasic action potential recordings from patients with AF was used to represent membrane kinetics in non-fibrotic myocardium. In fibrotic regions, further ionic modifications were implemented. At the tissue scale, fibrotic regions had reduced conductivities to represent impaired cell-to-cell coupling, as we have described previously. The rapid pacing atrial arrhythmia induction protocol is described on our previous publications, and involved rapid-pacing from 30 uniformly distributed locations on the LA. Simulations were performed in the CARP software package. Persistent RDs were identified using the wavefront tip analysis method. We also identified macro-reentrant atrial tachycardias (MAT), wavefront propagation around a non-conductive obstacle such as the mitral valve (MV) or pulmonary vein (PV).

Once the personalized simulations of AF induction in all 32 models were completed, features from the simulation results were selected for input into the ML classifier. These were chosen in two ways: i) by the authors based on general knowledge of AF dynamics (deductive features), and ii) by the ML training algorithm, unsupervised (inductive features). Deductive features included presence of RDs, theorized to correlate with or predict likelihood of AF recurrence, as well as other features we thought might be meaningful, such as the number of RDs inside the regions isolated by PVI. The latter could be predictive of AF recurrence in the case of PV reconnection, which has been shown to occur in as many as 85% of patients experiencing AF recurrence. In contrast, inductive features of the simulation results were "learned" in an unsupervised manner during classifier training by analyzing the simulation results in models of patients who experienced AF recurrence. This category of features was included to allow learning of predictive features of the simulation results not previously described in the literature and to reduce bias that may be introduced by hand-crafting the choice of features. Detail regarding the extraction of inductive features from the simulation results is below.

While LA models were based on LGE-MRI images, model reconstruction involved binarizing the fibrosis distribution via thresholding, as well as its interpolation and mapping to the 3D mesh. As unprocessed (raw) images of fibrosis distribution might contain additional prognostic information pertinent to AF recurrence, features from the LGE-MRI atrial scans were also made available to the classifier. The feature selection process was designed to pick the most important features while avoiding multicollinearity, so the classifier would not include features derived from LGE-MRI if the relevant predictive information was better encapsulated in features derived from the simulation results. The features included, among others, the heterogeneity and quantity of the fibrosis distribution, both suggested to correlate with AF propensity, and a fractal dimension-based feature which quantifies how quickly the complexity of the 3D surface of the fibrosis volume decreases as resolution decreases; the latter was calculated by analyzing the differences in the number of cubes of various sizes required to cover the entire surface of the fibrotic region.

Ten-fold nested cross-validation was used to train, validate, and test the classifier. Random forests were used for unbiased feature selection, then a QDA classifier was trained using the selected features to predict the probability of AF recurrence after PVI. Optimized hyperparameters included the number of features selected for the classifier and various parameters used to calculate the inductive simulation results features. The inductive simulation results features learned during training were recorded for further analysis. Further details regarding ML are provided below.

There were no significant differences in clinical characteristics, including several known AF risk factors, between patients who did and did not experience AF recurrence. Accordingly, we did not attempt to train classifiers with any of these clinical biomarkers as none of them were associated with AF recurrence.

Several examples of reconstructed LA models showing the patient-specific atrial geometries and fibrosis distributions, as well as examples of induced reentrant activity following the rapid pacing protocol in the models. A MAT was observed around the left inferior pulmonary vein (LIPV) in the LA model of Patient 1. An RD was found on the posterior left atrium adjacent to the MV in the LA model of patient 2. In the LA model of patient 3, RDs were found on the inferior posterior wall and LIPV, and a MAT perpetuated around the RIPV.

We first tested whether the simulation results themselves could be used to predict AF recurrence post-PVI. We found that reentry was induced from a larger number of pacing sites in the LA models of patients who experienced AF recurrence (9.2±1.8) compared to those of patients who did not (5.7±1.7), but this did not reach statistical significance (p=0.19). We also examined whether the number of pacing sites from which reentry was induced was associated with AF recurrence after PVI—the resulting AUC was 0.72. More RDs and MATs were observed in the models of patients who experienced AF recurrence (2.6±0.4) compared to those of patients who did not (1.7±0.4), but this also did not reach statistical significance (p=0.18). Using the number of pre-ablation simulated RDs and MATs to predict have AF recurrence after PVI, the AUC was 0.69 and the sensitivity and specificity were 75% and 60%. The lack of statistical significance in the hand-picked features and relatively low training AUCs indicates that this approach may not perform well when applied to previously unseen patients.

Our risk predictor, which used ML on features derived from both LGE-MRI imaging and the simulation results, predicted AF recurrence after PVI with an average validation sensitivity and specificity of 82% and 89%, respectively, and a validation AUC of 0.82. The training AUC was similar: 0.90. This indicates that the classifier is generalizable, or likely to correctly predict whether a previously unseen patient will experience AF recurrence after PVI, despite the small data set available for trainin.

When only features derived from the simulation results we used in an ML classifier, the predictive capability was similar: an average validation sensitivity and specificity of 79% and 89%, respectively, and a validation AUC of 0.81. This indicates that imaging features may not be necessary for an ML-based AF recurrence risk prediction, since removing them from feature selection did not significantly alter the validation sensitivity, specificity, or AUC.

In comparison, the validation sensitivity and specificity of an ML approach which used features derived directly from LGE-MRI were only 57% and 61% respectively. This classifier achieved a similar training AUC to the proposed methodology (0.85 vs. 0.90, respectively), but a much lower validation AUC (0.47 vs. 0.82, respectively), which implies that it was not generalizable. This suggests that a much larger data set would be required to train an ML classifier to correctly predict the AF recurrence risk of a previously unseen patient using only imaging features, further supporting the inclusion of the simulation results features in ML-based AF recurrence risk prediction.

To gain insight into how the ML classifier predicted AF recurrence after PVI, we analyzed the inductive simulation results features learned from the training data in each "outer loop" of cross-validation. The learned features of the simulation results (reentry locations and pacing locations) that were most predictive of AF recurrence and were thus selected by the ML classifier. All of the most predictive reentry-inducing pacing locations that contributed to the selected inductive simulation results features were outside the PVs. Additionally, the most predictive inductive features frequently involved the numbers of RDs and MATs on the LIPV and mid anterior wall, as well as the MV for MAT.

The goal of this study was to develop and evaluate a novel methodology for prediction of AF recurrence risk after PVI using ML and personalized mechanistic modeling of AF induction in the LA of patients with PxAF and fibrotic remodeling on LGE-MRI. We demonstrate that this approach results in a highly predictive and generalizable risk classifier, even when the patient cohort used to train the ML classifier is small. Our approach achieved an average validation sensitivity and specificity of 82% and 89%, respectively, and a validation AUC of 0.82, indicating that the classifier is generalizable and likely to accurately predict the AF risk of a previously unseen patient. To our knowledge, this is the first study to demonstrate that ML and mechanistic cardiac modeling can be used together to develop an accurate and generalizable classifier that predicts the risk of adverse clinical events.

Our ML-based AF recurrence risk prediction methodology incorporated both inductive simulation results features learned during training of the ML classifier and deductive simulation results features chosen prior to training. The inclusion of inductive features is analogous to deep learning, a popular form of ML in which feature extraction is performed in the process of training a classifier, rather than prior to training. Analysis of the inductive features defined during training confirms that the classifier can learn patterns of the simulation results which have not necessarily been previously evaluated for correlation with AF recurrence, but are clinically explainable in the context of published studies describing mechanisms of AF recurrence. For example, all pacing locations selected by the unsupervised inductive feature learning algorithm to calculate the most predictive inductive simulation results features were outside the PVs, which is supported by research suggesting that triggers outside the PVs contribute to recurrence.

Additionally, the most predictive inductive features involved the numbers of RDs and MATs on the LIPV and mid anterior wall, as well as the MV for MAT. Since the mid anterior wall and MV are outside the PV region and would not be electrically isolated by PVI, it is understandable that fibrosis distribution that can result in RDs and MATs located there would be highly predictive of AF recurrence. Furthermore, while it may seem counter-intuitive that reentry around the LIPV would predict AF recurrence, since PVI should electrically isolate this region, this feature might predict in which patients AF would recur should PV's reconnect after the ablation procedure. Found that re-connection of 1 or more PVs occurs in 85.5% of patients with AF recurrence, and 58.6% in patients without AF recurrence, which supports our findings. However, in order to confirm that, data will need to be collected on the mechanisms of clinical AF recurrence.

In designing this study, we hypothesized that an ML classifier which included features derived from both the simulation results and imaging would provide the best prediction of AF recurrence after PVI. However, we found that removing imaging features from the input to feature selection for the ML classifier did not decrease its predictive capability. In addition, the classifier which only included features derived from imaging achieved a much lower validation AUC than training AUC, indicating that a larger data set would likely be needed to increase the generalizability of the classifier, i.e. the ability of the classifier to correctly predict the AF recurrence risk of a previously unseen patient from imaging data only. Thus, our results demonstrated that the imaging features do not provide additional predictive value and may not be necessary for our proposed ML-based AF recurrence risk prediction methodology, which implies that the relevant predictive information from LGE-MRI is encapsulated in the LA models.

The validation AUC of the classifier which included only features derived from the simulation results to predict AF recurrence was higher than the AUCs achieved using measures of AF inducibility in the LA models without ML. While both risk prediction methods relied on the same underlying simulation results in the same LA models, the ML classifier training algorithm allowed selection of multiple features derived from the simulation results and weighting of these features, so the resulting classifier was finely tuned. In contrast, the non-ML method predicted the risk of AF recurrence via thresholding of a single measure of AF propensity (number of reentry locations or number of reentry-inducing pacing sites); it did not consider multiple features, their relative importance, or inductive features learned from the training data.

A limitation of this study is the small data set, often a serious concern in ML studies. However, by using 10-fold nested cross-validation and aggregating the results, we demonstrated nonetheless excellent predictive capability. The proposed combined approach achieved similarly high validation and training AUCs, indicating that the resulting classifier was generalizable despite the small data set. Prospective validation in a larger cohort would confirm the predictive capability of the proposed AF risk prediction methodology. Another limitation is the lack of published detailed methods and quantitative results for previously proposed imaging-based ML risk prediction methodologies, which limited our ability to compare these with our methodology. A recent approach which used only imaging features achieved a F1-score (harmonic mean of precision and recall) of 0.33, while our approach achieved a testing F1-score of 0.70. However, the study did not state what part of the data (training, testing, or validation) this F1-score applied to, so this may be a poor comparison. Further, two clinical risk scores have been proposed to predict the risk of AF recurrence after PVI: the ATLAS score and the CAAP-AF score, but our retrospective registry did not contain all the necessary variables to calculate either of these risk scores. However, we note that our ML classifier achieved a validation AUC of 0.82, which is greater than the censored C-statistic of 0.75 achieved by the ATLAS score and the development AUC of 0.69 achieved by the CAAP-AF score.

In this study, we developed an AF recurrence risk prediction methodology that used ML and personalized mechanistic modeling together and demonstrated that it can accurately predict whether a patient is likely to experience AF recurrence after PVI in patients with PxAF and fibrosis on LGE-MRI. The resulting classifier considers the potential patient-specific mechanisms of arrhythmogenesis resulting from the fibrotic substrate in the LA, making it clinically explainable. To our knowledge, this is the first study to demonstrate the potential of combining computational cardiac modeling and ML to make clinical predictions.

For the purpose of extracting inductive features of the simulation results, the left atrium (LA) was divided into 11 anatomical regions: base, inferior posterior LA, left of the posterior LA, left atrial appendage, left inferior pulmonary vein, left superior pulmonary vein, mitral valve, mid anterior LA, mid posterior LA, right inferior pulmonary vein, and right superior pulmonary vein. In each patient-specific LA model, we recorded the pacing sites from which sustained AF was induced and the regions where RD or MAT were localized.

The inductive simulation results features were defined via analysis of the training data, then calculated for the training and validation or test data for the inner and outer loops of cross-validation, respectively. They were learned in an unsupervised manner as follows: for each LA model in the training data set and each of the 11 anatomical regions in that model, 6 characteristics of the simulation results were computed: the number of RDs (nRD), MATS (nMAT), and reentries (nRD+MAT) located in the given region, and the proportions of pacing sites in the region (out of the total number of pacing sites) from which RD (pRD), MAT (pMAT), or a reentry (pRD+MAT) was induced. For each characteristic of the simulation results, the differences between patients who did and did not experience AF for each of the 11 anatomical regions were ranked in significance with the Wilcoxon rank sum test. Several anatomical regions with the highest significance were chosen in the calculation of each inductive feature for the training and validation/test sets. The numbers of anatomical regions selected from the ranked list for feature calculation were treated as hyperparameters and were optimized as described in the following section.

Ten-fold nested cross-validation was used to train, validate, and test the AF recurrence risk classifier. In each fold of the "outer loop" of cross-validation, 10% of the data was set aside to use as a test set. The remaining 90% were used for validation and training in the "inner loop" of cross validation. In each fold of the "inner loop", 10% of the data was set aside for validation. The remaining 90% were used to train QDA classifiers with weighted loss to account for any class imbalance in the training data. Hyperparameters of the classifier included the number of features selected and the numbers of anatomical regions used in the calculation of the various inductive simulation features.

In each fold of cross-validation, feature selection was performed using a random forest developed with the training data set, which consisted of out-of-bag permuted predictor importance estimates using a bagged ensemble of 300 regression trees. For each tree in the forest, feature selection was performed with the interaction-curvature test, which chose the split predictor that minimized the p-value of chi-square tests of independence between each feature and the outcome, and that minimized the p-value of a chi-square test of independence between each pair of features and the outcome. The outcome was a binary value indicating whether a given patient experienced AF recurrence. Feature importance for each predictor was determined by randomly permuting predictor values for each tree and observing the effect on the classification error.

In the "inner loop" of cross-validation, a grid search was used to find the optimal hyperparameters by training QDA classifiers with all possible combinations of the following: K features of highest importance ($1 \leq K \leq 5$), N anatomical regions for inductive simulation results features that involved specific reentry locations (nRD, nMAT, and nRD+MAT; $1 \leq N \leq 4$), and P anatomical regions for inductive simulation results features that involve specific pacing locations (pRD, pMAT, and pRD+MAT; $1 \leq P \leq 4$). Each trained QDA classifier was then used to predict the probability of AF recurrence for the validation set. Following the "inner loop", the hyperparameters which maximized the area under the validation receiver operating characteristic (ROC) curve (AUC), were selected and used to train a classifier with all the patients from the inner loop.

The trained QDA classifier with optimal hyperparameters was used to predict the probability of AF recurrence for the left-out test set. Training, validation, and testing results were aggregated over all loops of cross-validation to create training and validation ROC curves.

Figure 2:
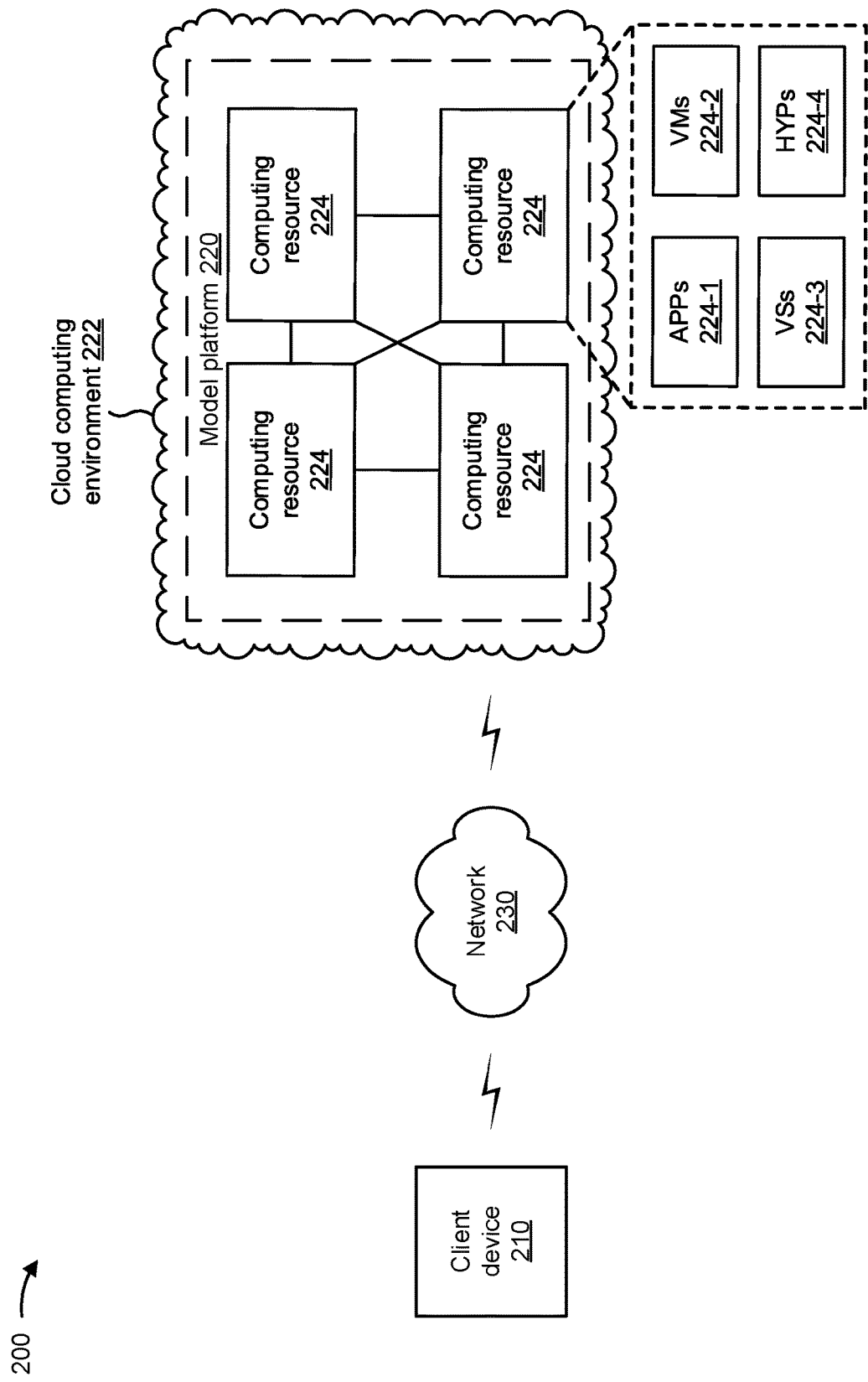
FIG. 2 is a diagram of an example environment in which systems and/or methods described herein may be implemented.

FIG. 2 is a diagram of an example environment 200 in which systems and/or methods described herein may be implemented. As shown in FIG. 2, environment 200 may include a client device 210, a model platform 220, and a network 230. Devices of environment 200 may interconnect via wired connections, wireless connections, or a combination of wired and wireless connections.

Client device 210 includes one or more devices capable of receiving, generating, storing, processing, and/or providing information, such as information described herein. For example, client device 210 may include a mobile phone (e.g., a smart phone, a radiotelephone, and/or the like), a laptop computer, a tablet computer, a desktop computer, a handheld computer, a set-top box, a gaming device, a wearable communication device (e.g., a smart watch, a pair of smart glasses, a heart rate monitor, a fitness tracker, smart clothing, smart jewelry, a head mounted display, and/or the like), a device with a sensor (e.g., a light sensor, a temperature sensor, a power sensor, and/or the like), or a similar type of device. In some implementations, client device 210 may receive information from and/or transmit information to model platform 220.

Model platform 220 includes one or more devices that predict atrial fibrillation recurrence after pulmonary vein isolation using simulations of patient-specific magnetic resonance imaging models and machine learning. In some implementations, model platform 220 may be designed to be modular such that certain software components may be swapped in or out depending on a particular need. As such, model platform 220 may be easily and/or quickly reconfigured for different uses. In some implementations, model platform 220 may receive information from and/or transmit information to one or more client devices 210.

In some implementations, as shown, model platform 220 may be hosted in a cloud computing environment 222. Notably, while implementations described herein describe model platform 220 as being hosted in cloud computing environment 222 (e.g., a data center), in some implementations, model platform 220 may not be cloud-based (i.e., may be implemented outside of a cloud computing environment) or may be partially cloud-based.

Cloud computing environment 222 includes an environment that hosts model platform 220. Cloud computing environment 222 may provide computation, software, data access, storage, etc., services that do not require end-user knowledge of a physical location and configuration of system(s) and/or device(s) that host model platform. As shown, cloud computing environment 222 may include a group of computing resources 224 (referred to collectively as "computing resources 224" and individually as "computing resource 224").

Computing resource 224 includes one or more personal computers, workstation computers, mainframe devices, or other types of computation and/or communication devices. In some implementations, computing resource 224 may host model platform 220. The cloud resources may include compute instances executing in computing resource 224, storage devices provided in computing resource 224, data transfer devices provided by computing resource 224, etc. In some implementations, computing resource 224 may communicate with other computing resources 224 via wired connections, wireless connections, or a combination of wired and wireless connections.

As further shown in FIG. 2, computing resource 224 includes a group of cloud resources, such as one or more applications ("APPs") 224-1, one or more virtual machines ("VMs") 224-2, virtualized storage ("VSs") 224-3, one or more hypervisors ("HYPs") 224-4, and/or the like.

Application 224-1 includes one or more software applications that may be provided to or accessed by client device 210. Application 224-1 may eliminate a need to install and execute the software applications on client device 210. For example, application 224-1 may include software associated with model platform 220 and/or any other software capable of being provided via cloud computing environment 222. In some implementations, one application 224-1 may send/receive information to/from one or more other applications 224-1, via virtual machine 224-2.

Virtual machine 224-2 includes a software implementation of a machine (e.g., a computer) that executes programs like a physical machine. Virtual machine 224-2 may be either a system virtual machine or a process virtual machine, depending upon use and degree of correspondence to any real machine by virtual machine 224-2. A system virtual machine may provide a complete system platform that supports execution of a complete operating system. A process virtual machine may execute a single program and may support a single process. In some implementations, virtual machine 224-2 may execute on behalf of a user (e.g., a user of client device 210 or an operator of model platform 220), and may manage infrastructure of cloud computing environment 222, such as data management, synchronization, or long-duration data transfers.

Virtualized storage 224-3 includes one or more storage systems and/or one or more devices that use virtualization techniques within the storage systems or devices of computing resource 224. In some implementations, within the context of a storage system, types of virtualizations may include block virtualization and file virtualization. Block virtualization may refer to abstraction (or separation) of logical storage from physical storage so that the storage system may be accessed without regard to physical storage or heterogeneous structure. The separation may permit administrators of the storage system flexibility in how the administrators manage storage for end users. File virtualization may eliminate dependencies between data accessed at a file level and a location where files are physically stored. This may enable optimization of storage use, server consolidation, and/or performance of non-disruptive file migrations.

Hypervisor 224-4 may provide hardware virtualization techniques that allow multiple operating systems (e.g., "guest operating systems") to execute concurrently on a host computer, such as computing resource 224. Hypervisor 224-4 may present a virtual operating platform to the guest operating systems and may manage the execution of the guest operating systems. Multiple instances of a variety of operating systems may share virtualized hardware resources.

Network 230 includes one or more wired and/or wireless networks. For example, network 230 may include a cellular network (e.g., a fifth generation (5G) network, a long-term evolution (LTE) network, a third generation (3G) network, a code division multiple access (CDMA) network, etc.), a public land mobile network (PLMN), a local area network (LAN), a wide area network (WAN), a metropolitan area network (MAN), a telephone network (e.g., the Public Switched Telephone Network (PSTN)), a private network, an ad hoc network, an intranet, the Internet, a fiber optic-based network, and/or the like, and/or a combination of these or other types of networks. In some implementations, network 230 may receive information from and/or transmit information to client device 210 and/or model platform 220.

The number and arrangement of devices and networks shown in FIG. 2 are provided as an example. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 200 may perform one or more functions described as being performed by another set of devices of environment 200.

Figure 3:
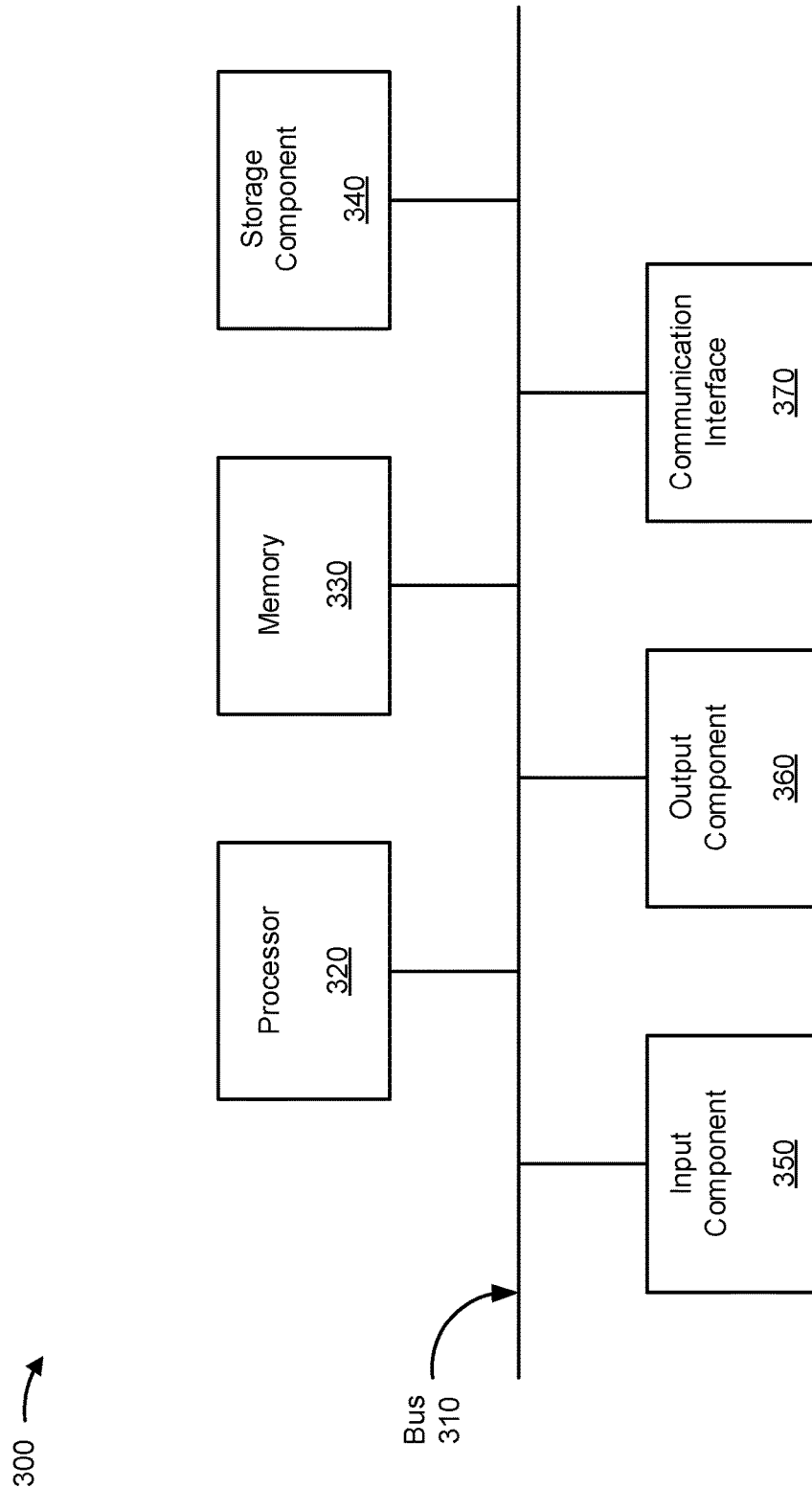
FIG. 3 is a diagram of example components of one or more devices of FIG. 2.

FIG. 3 is a diagram of example components of a device 300. Device 300 may correspond to client device 210, model platform 220, and/or computing resource 224. In some implementations, client device 210, model platform 220, and/or computing resource 224 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random-access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid-state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more light-emitting diodes (LEDs)).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a Wi-Fi interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
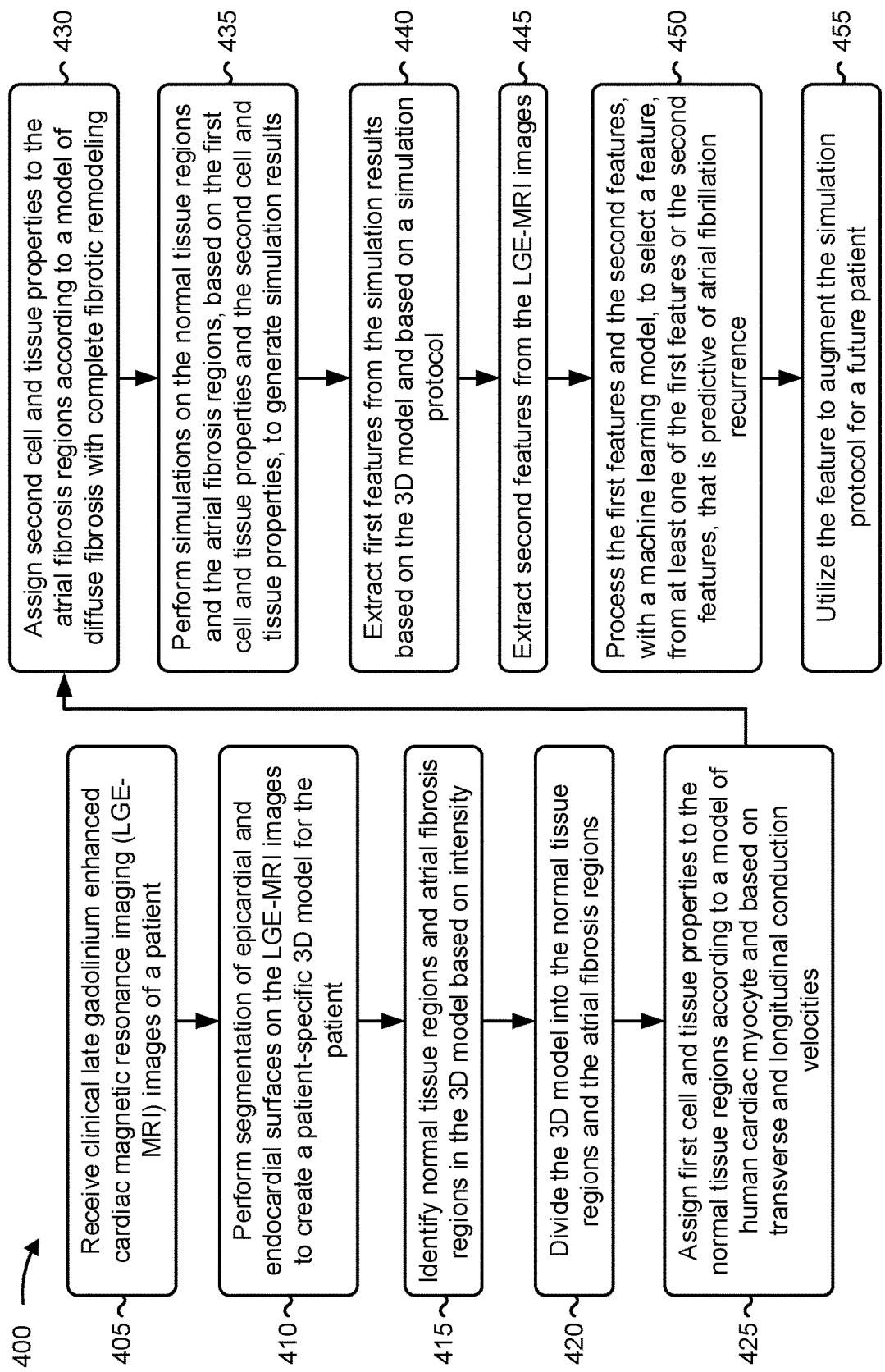
FIG. 4 is a flow chart of example processes for predicting atrial fibrillation recurrence after pulmonary vein isolation using simulations of patient-specific magnetic resonance imaging models and machine learning.

FIG. 4 is a flow chart of an example process 400 for predicting atrial fibrillation recurrence after pulmonary vein isolation using simulations of patient-specific magnetic resonance imaging models and machine learning. In some implementations, one or more process blocks of FIG. 4 may be performed by a device (e.g., model platform 220). In some implementations, one or more process blocks of FIG. 4 may be performed by another device or a group of devices separate from or including the device, such as a client device (e.g., client device 210).

As shown in FIG. 4, process 400 may include receiving clinical late gadolinium enhanced cardiac magnetic resonance imaging (LGE-MRI) images of a patient (block 405). For example, the device (e.g., using computing resource 224, processor 320, communication interface 370, and/or the like) may receive clinical late gadolinium enhanced cardiac magnetic resonance imaging (LGE-MRI) images of a patient, as described above.

As further shown in FIG. 4, process 400 may include performing segmentation of epicardial and endocardial surfaces on the LGE-MRI images to create a patient-specific three-dimensional (3D) model for the patient (block 410). For example, the device (e.g., using computing resource 224, processor 320, memory 330, and/or the like) may perform segmentation of epicardial and endocardial surfaces on the LGE-MRI images to create a patient-specific three-dimensional (3D) model for the patient, as described above.

As further shown in FIG. 4, process 400 may include identifying normal tissue regions and atrial fibrosis regions in the 3D model based on intensity (block 415). For example, the device (e.g., using computing resource 224, processor 320, storage component 340, and/or the like) may identify normal tissue regions and atrial fibrosis regions in the 3D model based on intensity, as described above.

As further shown in FIG. 4, process 400 may include dividing the 3D model into the normal tissue regions and the atrial fibrosis regions (block 420). For example, the device (e.g., using computing resource 224, processor 320, memory 330, and/or the like) may divide the 3D model into the normal tissue regions and the atrial fibrosis regions, as described above.

As further shown in FIG. 4, process 400 may include assigning first cell and tissue properties to the normal tissue regions according to a model of human cardiac myocyte and based on transverse and longitudinal conduction velocities (block 425). For example, the device (e.g., using computing resource 224, processor 320, storage component 340, and/or the like) may assign first cell and tissue properties to the normal tissue regions according to a model of human cardiac myocyte and based on transverse and longitudinal conduction velocities, as described above.

As further shown in FIG. 4, process 400 may include assigning second cell and tissue properties to the atrial fibrosis regions according to a model of diffuse fibrosis with complete fibrotic remodeling (block 430). For example, the device (e.g., using computing resource 224, processor 320, memory 330, storage component 340, and/or the like) may assign second cell and tissue properties to the atrial fibrosis regions according to a model of diffuse fibrosis with complete fibrotic remodeling, as described above.

As further shown in FIG. 4, process 400 may include performing simulations on the normal tissue regions and the atrial fibrosis regions, based on the first cell and tissue properties and the second cell and tissue properties, to generate simulation results (block 435). For example, the device (e.g., using computing resource 224, processor 320, memory 330, and/or the like) may perform simulations on the normal tissue regions and the atrial fibrosis regions, based on the first cell and tissue properties and the second cell and tissue properties, to generate simulation results, as described above.

As further shown in FIG. 4, process 400 may include extracting first features from the simulation results based on the 3D model and based on a simulation protocol (block 440). For example, the device (e.g., using computing resource 224, processor 320, storage component 340, and/or the like) may extract first features from the simulation results based on the 3D model and based on a simulation protocol, as described above.

As further shown in FIG. 4, process 400 may include extracting second features from the LGE-MRI images (block 445). For example, the device (e.g., using computing resource 224, processor 320, memory 330, storage component 340, and/or the like) may extract second features from the LGE-MRI images, as described above.

As further shown in FIG. 4, process 400 may include processing the first features and the second features, with a machine learning model, to select a feature, from at least one of the first features or the second features, that is predictive of atrial fibrillation recurrence (block 450). For example, the device (e.g., using computing resource 224, processor 320, memory 330, and/or the like) may process the first features and the second features, with a machine learning model, to select a feature, from at least one of the first features or the second features, that is predictive of atrial fibrillation recurrence, as described above.

As further shown in FIG. 4, process 400 may include utilizing the feature to augment the simulation protocol for a future patient (block 455). For example, the device (e.g., using computing resource 224, processor 320, memory 330, storage component 340, communication interface 370, and/or the like) may utilize the feature to augment the simulation protocol for a future patient, as described above.

Process 400 may include additional implementations, such as any single implementation or any combination of implementations described below and/or in connection with one or more other processes described elsewhere herein.

In a first implementation, process 400 may include assigning myocardial fiber orientations based on the 3D model for the patient.

In a second implementation, alone or in combination with the first implementation, processing the first features and the second features, with a machine learning model, to select the feature may include selecting the feature based on minimizing an overfit of a data set of the first features and the second features.

In a third implementation, alone or in combination with one or more of the first and second implementations, process 400 may include utilizing the feature to predict whether isolation of pulmonary veins will be successful and whether additional lesions are needed in an atria of the future patient.

In a fourth implementation, alone or in combination with one or more of the first through third implementations, process 400 may include processing the first features and the second features, with another machine learning model, to determine a sorted order for the first features and the second features based on importance in predicting catheter ablation efficiency; and utilizing the sorted order to predict catheter ablation efficiency for the future patient.

In a fifth implementation, alone or in combination with one or more of the first through fourth implementations, performing the segmentation of the epicardial and endocardial surfaces on the LGE-MRI images to create the patient-specific 3D model may include processing the epicardial and endocardial surfaces on the LGE-MRI images, with an automatic segmentation model or a semi-automatic segmentation model, to create the patient-specific 3D model.

In a sixth implementation, alone or in combination with one or more of the first through fifth implementations, the machine learning model may include a random forest, with k-fold cross validation, model.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

The foregoing disclosure provides illustration and description, but is not intended to be exhaustive or to limit the implementations to the precise form disclosed. Modifications and variations may be made in light of the above disclosure or may be acquired from practice of the implementations.

As used herein, the term "component" is intended to be broadly construed as hardware, firmware, or a combination of hardware and software.

It will be apparent that systems and/or methods described herein may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
   receiving, by a device, clinical late gadolinium enhanced cardiac magnetic resonance imaging (LGE-MRI) images of a patient;
   performing, by the device, segmentation of epicardial and endocardial surfaces on the LGE-MRI images to create a patient-specific three-dimensional (3D) model for the patient;
   identifying, by the device, normal tissue regions and atrial fibrosis regions in the 3D model based on intensity;
   dividing, by the device, the 3D model into the normal tissue regions and the atrial fibrosis regions;
   assigning, by the device, first cell and tissue properties to the normal tissue regions according to a model of human cardiac myocyte and based on transverse and longitudinal conduction velocities;
   assigning, by the device, second cell and tissue properties to the atrial fibrosis regions according to a model of diffuse fibrosis with complete fibrotic remodeling;
   performing, by the device, simulations on the normal tissue regions and the atrial fibrosis regions, based on the first cell and tissue properties and the second cell and tissue properties, to generate simulation results;
   extracting, by the device, first features from the simulation results based on the 3D model and based on a simulation protocol;
   extracting, by the device, second features from the LGE-MRI images;
   processing, by the device, the first features and the second features, with a machine learning model, to select a feature, from at least one of the first features or the second features, that is predictive of atrial fibrillation recurrence; and
   utilizing, by the device, the feature to augment the simulation protocol for a future patient.

2. The method of claim 1, further comprising:
   assigning myocardial fiber orientations based on the 3D model for the patient.

3. The method of claim 1, wherein processing the first features and the second features, with a machine learning model, to select the feature comprises:
   selecting the feature based on minimizing an overfit of a data set of the first features and the second features.

4. The method of claim 1, further comprising:
   utilizing the feature to predict whether isolation of pulmonary veins will be successful and whether additional lesions are needed in an atria of the future patient.

5. The method of claim 1, further comprising:
   process the first features and the second features, with another machine learning model, to determine a sorted order for the first features and the second features based on importance in predicting catheter ablation efficiency; and
   utilizing the sorted order to predict catheter ablation efficiency for the future patient.

6. The method of claim 1, wherein performing the segmentation of the epicardial and endocardial surfaces on the LGE-MRI images to create the patient-specific 3D model comprises:
   processing the epicardial and endocardial surfaces on the LGE-MRI images, with an automatic segmentation model or a semi-automatic segmentation model, to create the patient-specific 3D model.

7. The method of claim 1, wherein the machine learning model includes a random forest, with k-fold cross validation, model.

8. A device, comprising:
one or more memories; and
one or more processors, communicatively coupled to the one or more memories, configured to:
receive clinical late gadolinium enhanced cardiac magnetic resonance imaging (LGE-MRI) images of a patient;
perform segmentation of epicardial and endocardial surfaces on the LGE-MRI images to create a patient-specific three-dimensional (3D) model for the patient;
identify normal tissue regions and atrial fibrosis regions in the 3D model based on intensity;
divide the 3D model into the normal tissue regions and the atrial fibrosis regions;
assign first cell and tissue properties to the normal tissue regions according to a model of human cardiac myocyte and based on transverse and longitudinal conduction velocities;
assign second cell and tissue properties to the atrial fibrosis regions according to a model of diffuse fibrosis with complete fibrotic remodeling;
perform simulations on the normal tissue regions and the atrial fibrosis regions, based on the first cell and tissue properties and the second cell and tissue properties, to generate simulation results;
extract first features from the simulation results based on the 3D model and based on a simulation protocol;
extract second features from the LGE-MRI images;
process the first features and the second features, with a machine learning model, to select a feature, from at least one of the first features or the second features, that is predictive of atrial fibrillation recurrence; and
utilize the feature to augment the simulation protocol for a future patient.

9. The device of claim 8, wherein the one or more processors are further configured to:
assign myocardial fiber orientations based on the 3D model for the patient.

10. The device of claim 8, wherein the one or more processors, when processing the first features and the second features, with a machine learning model, to select the feature, are configured to:
select the feature based on minimizing an overfit of a data set of the first features and the second features.

11. The device of claim 8, wherein the one or more processors are further configured to:
utilize the feature to predict whether isolation of pulmonary veins will be successful and whether additional lesions are needed in an atria of the future patient.

12. The device of claim 8, wherein the one or more processors are further configured to:
process the first features and the second features, with another machine learning model, to determine a sorted order for the first features and the second features based on importance in predicting catheter ablation efficiency; and
utilize the sorted order to predict catheter ablation efficiency for the future patient.

13. The device of claim 8, wherein the one or more processors, when performing the segmentation of the epicardial and endocardial surfaces on the LGE-MRI images to create the patient-specific 3D model, are configured to:
process the epicardial and endocardial surfaces on the LGE-MRI images, with an automatic segmentation model or a semi-automatic segmentation model, to create the patient-specific 3D model.

14. The device of claim 8, wherein the machine learning model includes a random forest, with k-fold cross validation, model.

15. A non-transitory computer-readable medium storing instructions, the instructions comprising:
one or more instructions that, when executed by one or more processors, cause the one or more processors to:
receive clinical late gadolinium enhanced cardiac magnetic resonance imaging (LGE-MRI) images of a patient;
perform segmentation of epicardial and endocardial surfaces on the LGE-MRI images to create a patient-specific three-dimensional (3D) model for the patient;
identify normal tissue regions and atrial fibrosis regions in the 3D model based on intensity;
divide the 3D model into the normal tissue regions and the atrial fibrosis regions;
assign first cell and tissue properties to the normal tissue regions according to a model of human cardiac myocyte and based on transverse and longitudinal conduction velocities;
assign second cell and tissue properties to the atrial fibrosis regions according to a model of diffuse fibrosis with complete fibrotic remodeling;
perform simulations on the normal tissue regions and the atrial fibrosis regions, based on the first cell and tissue properties and the second cell and tissue properties, to generate simulation results;
extract first features from the simulation results based on the 3D model and based on a simulation protocol;
extract second features from the LGE-MRI images;
process the first features and the second features, with a machine learning model, to select a feature, from at least one of the first features or the second features, that is predictive of atrial fibrillation recurrence; and
utilize the feature to augment the simulation protocol for a future patient.

16. The non-transitory computer-readable medium of claim 15, wherein the one or more instructions, when executed by the one or more processors, further cause the one or more processors to:
assign myocardial fiber orientations based on the 3D model for the patient.

17. The non-transitory computer-readable medium of claim 15, wherein the one or more instructions, that cause the one or more processors to process the first features and the second features, with a machine learning model, to select the feature, cause the one or more processors to:
select the feature based on minimizing an overfit of a data set of the first features and the second features.

18. The non-transitory computer-readable medium of claim 15, wherein the one or more instructions, when executed by the one or more processors, further cause the one or more processors to:
utilize the feature to predict whether isolation of pulmonary veins will be successful and whether additional lesions are needed in an atria of the future patient.

19. The non-transitory computer-readable medium of claim 15, wherein the one or more instructions, when executed by the one or more processors, further cause the one or more processors to:

process the first features and the second features, with another machine learning model, to determine a sorted order for the first features and the second features based on importance in predicting catheter ablation efficiency; and utilize the sorted order to predict catheter ablation efficiency for the future patient.

20. The non-transitory computer-readable medium of claim 15, wherein the one or more instructions, that cause the one or more processors to perform the segmentation of the epicardial and endocardial surfaces on the LGE-MRI images to create the patient-specific 3D model, cause the one or more processors to:

process the epicardial and endocardial surfaces on the LGE-MRI images, with an automatic segmentation model or a semi-automatic segmentation model, to create the patient-specific 3D model.

* * * * *